(12) United States Patent
Lantz et al.

(10) Patent No.: US 7,829,289 B2
(45) Date of Patent: Nov. 9, 2010

(54) T CELL SUBPOPULATION REGULATING GUT IMMUNITY

(75) Inventors: Olivier Lantz, Paris (FR); Emmanuel Treiner, Paris (FR)

(73) Assignees: Institut National de la Sante et de Recherche Medicale, Paris Cedex (FR); Institut Curie, Paris Cedex (FR)

( * ) Notice: Subject to any disclaimer, the term of this patent is extended or adjusted under 35 U.S.C. 154(b) by 1368 days.

(21) Appl. No.: 10/143,822

(22) Filed: May 14, 2002

(65) Prior Publication Data

US 2003/0215808 A1    Nov. 20, 2003

(51) Int. Cl.
C12Q 1/02     (2006.01)
C12Q 1/68     (2006.01)
G01N 33/566   (2006.01)

(52) U.S. Cl. .................. 435/7.1; 435/6; 435/7.2; 435/7.24; 435/7.8; 435/29; 436/501

(58) Field of Classification Search ............. 435/6, 435/7.1, 7.2, 7.24, 7.8, 29; 436/501
See application file for complete search history.

(56) References Cited

U.S. PATENT DOCUMENTS

2003/0215808 A1* 11/2003 Lantz et al. .............. 435/6

OTHER PUBLICATIONS

Treiner et al, "The phylogenetically conserved Vα19-Jα33 T cell subpopulation: selection , localization and ligand recognition" Abstract SFI Nov. 2001 SFI—Annual Congress of the French Society of Immunology, Paris, Nov. 21-23, 2001.
Treiner et al, "The phylogenetically conserved Vα19-Jα33 T cell subpopulation: selection, localization and ligand recognition", Keystone Symposia—"Innate Immunity : Evolution and link to adaptive immunity", Feb. 3-9, 2002, Taos NM.
Riegert et al "Genomics, Isoforms, Expression, and Phylogeny of the MHC Class I-related MR1 Gene" The Journal of Immunology, 1998, 161:4066-4077.
Badr-el-Din et al, "Local immunity in ulcerative colitis: evidence for defective secretory IgA production", Gut. 1988, August; 29(8):1070-5 (Abstract).
Cicalese et al, "Decreased mucosal IgA levels in ileum of patients with chronic ulcerative colitis", Dig Dis Sci. Apr. 1995; 40(4):805-11 (Abstract).
Marteau et al, "Immunological study of histologically non-involved jejunum during Crohn's disease: evidence for reduced in vivo secretion of secretory IgA", Clin Exp Immunol. May 1990; 80(2):196-201 (Abstract).
Mestecky et al., "Intestinal IgA: novel views on its function in the defence of the largest mucosal surface", Gut, 1999, 44:2-5.
Stevceva et al, "the inflammatory infiltrate in the acute stage of the dextran sulphate sodium induced colitis: B cell response differs depending on the percentage of DSS used to induct it", BMC Clinical Pathology, 2001, 1:3.
Definition—Inflammatory Bowel Disease—MeSH—NCBI web site—printed Mar. 17, 2007.

* cited by examiner

Primary Examiner—David A Saunders
(74) Attorney, Agent, or Firm—Nixon & Vanderhye P.C.

(57) ABSTRACT

The invention relates to methods of modulating an immune response in a mammal by modulating the activity of Jα33 T cells or of MR1 polypeptide in vitro, ex vivo or in vivo. The invention also relates to methods of regulating the activity of immune cells, particularly of T lymphocytes and/or B lymphocytes by regulating the activity of MR1 in vitro, ex vivo or in vivo. The invention further comprises methods of screening active compounds using MR1 or fragments thereof, or nucleic acid encoding the same, or recombinant host cells expressing said polypeptide. The invention also deals with a pharmaceutical composition comprising Jα33 T cells, MR1 polypeptide or a compound that modulates the activity of Jα33 TCR T cells or of MR1 polypeptide and a pharmaceutically acceptable vehicle or carrier. The invention further deals with methods of diagnosis for intestinal diseases related to a defect of the activity of said Jα33 T cells or MR1 polypeptide.

5 Claims, 27 Drawing Sheets

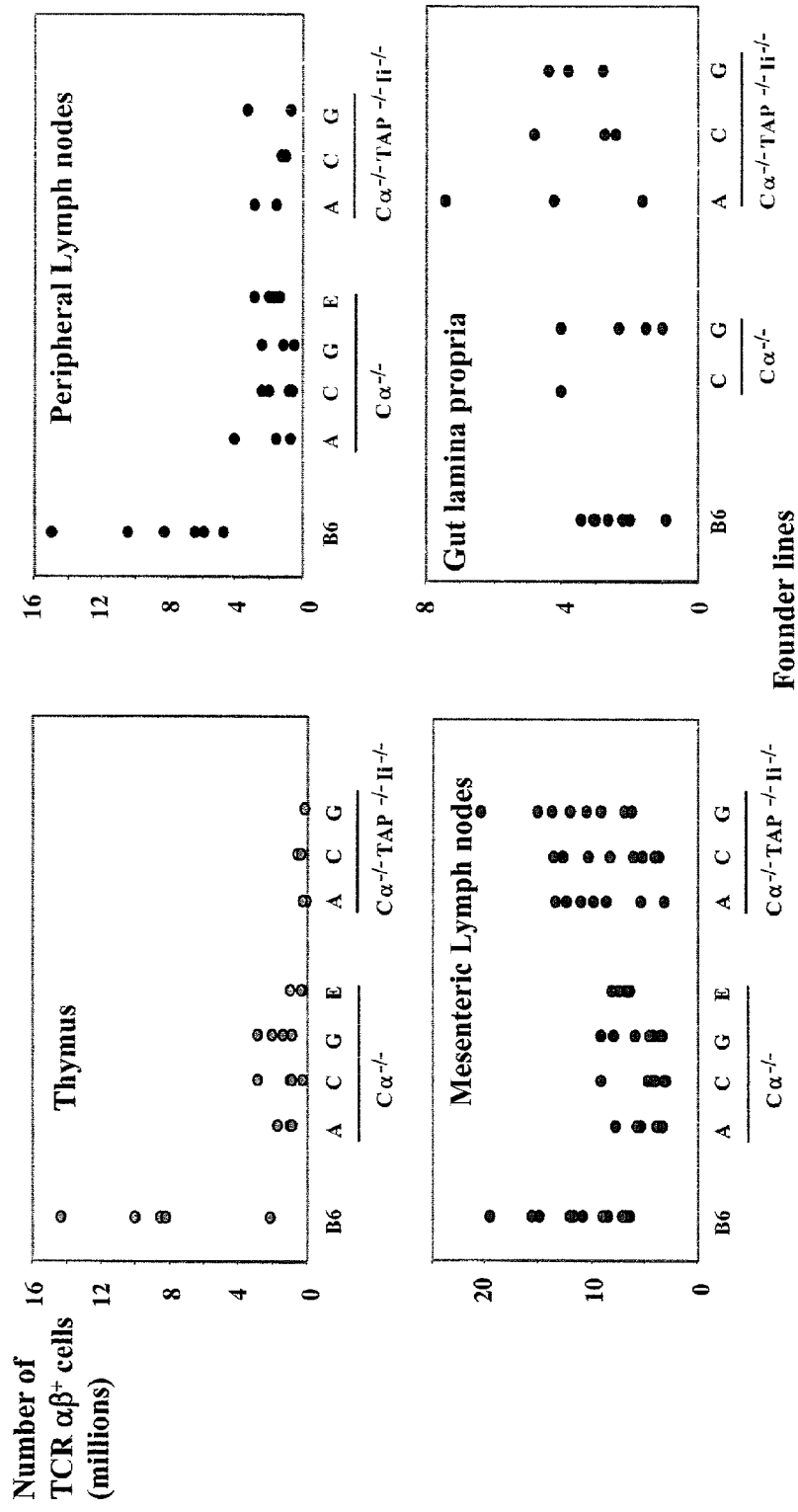

Figure 1A:
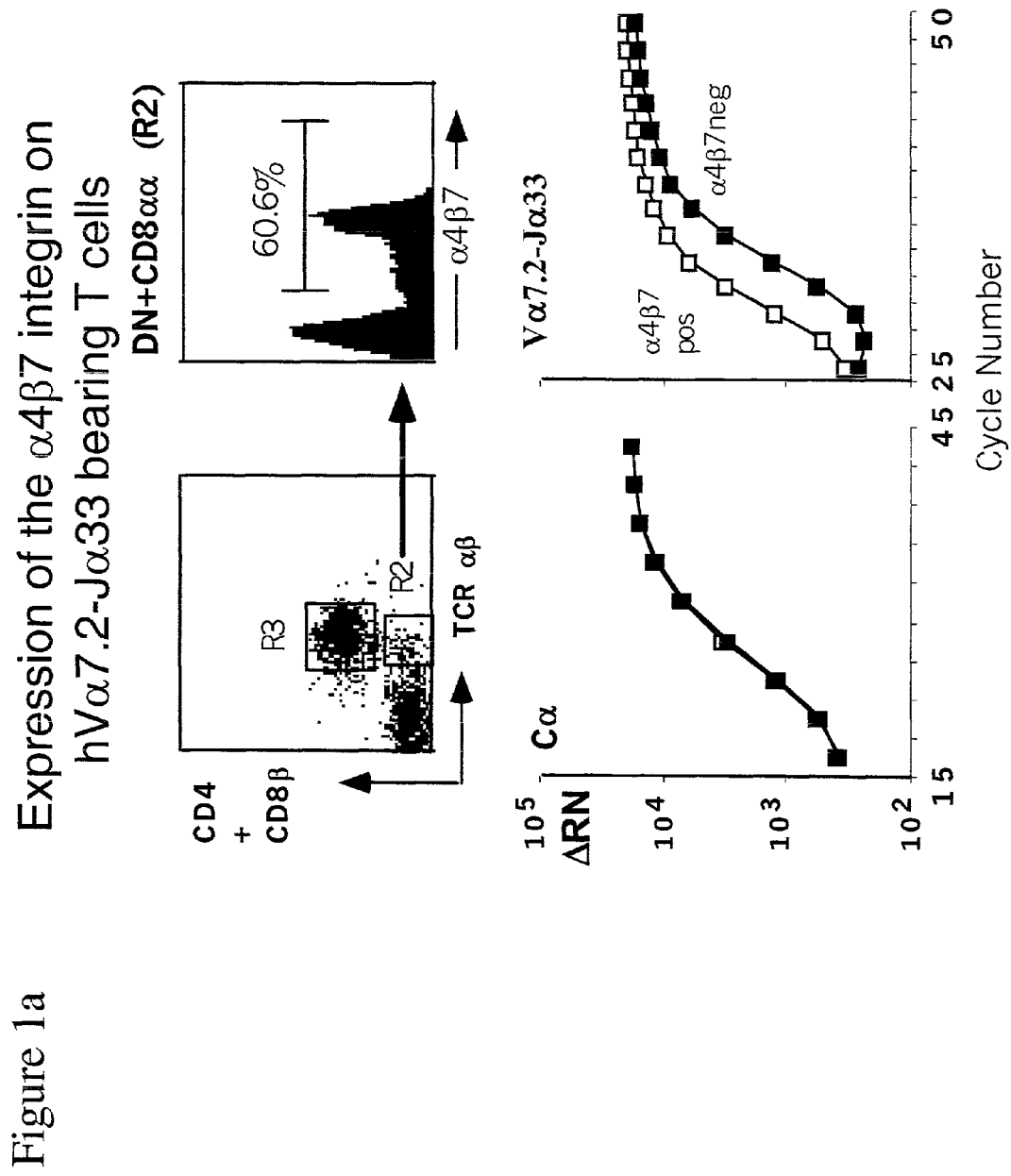

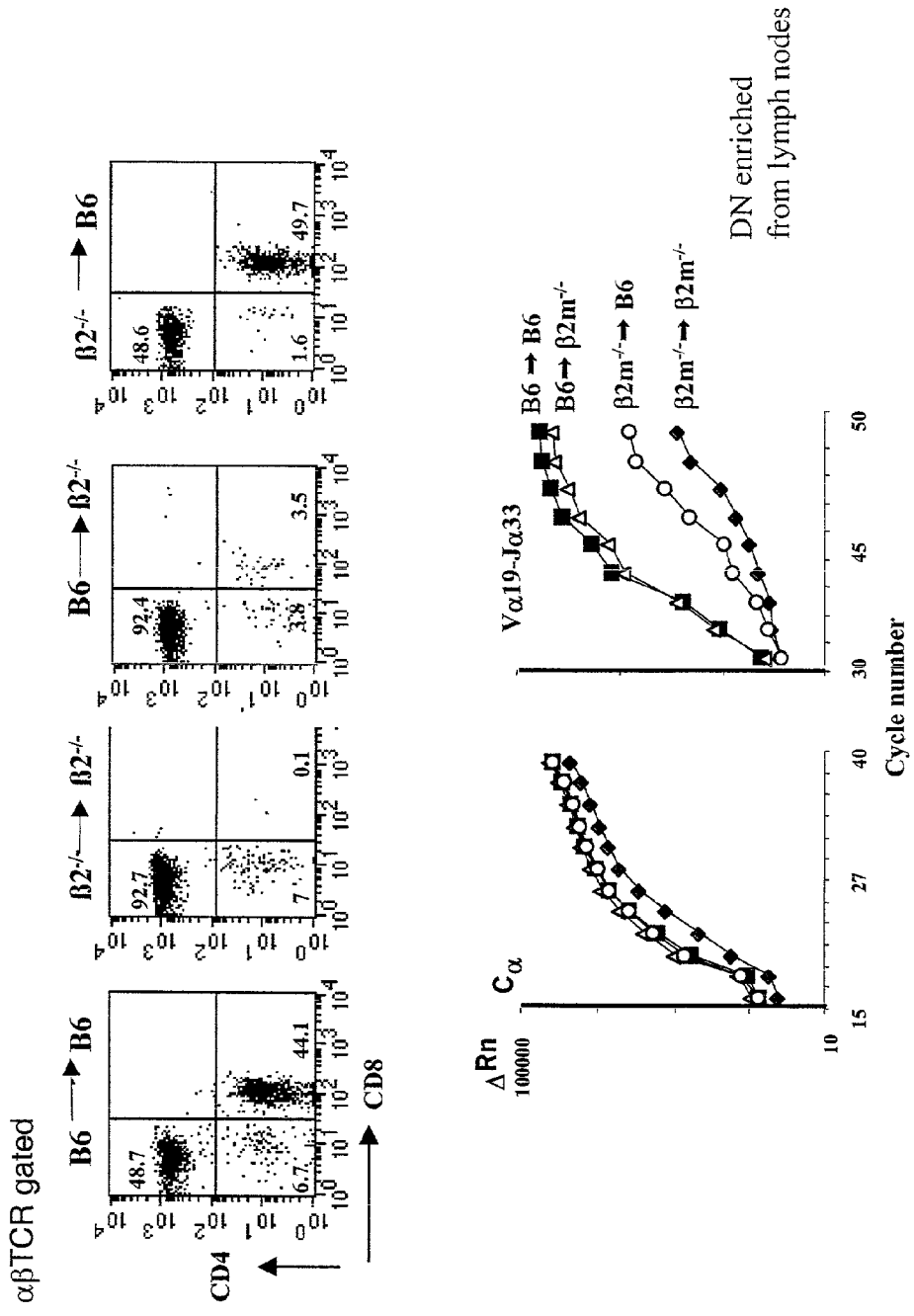
Fig. 3A  The selection of Vα19+ T cells requires the expression of their ligand on hematopoietic cells

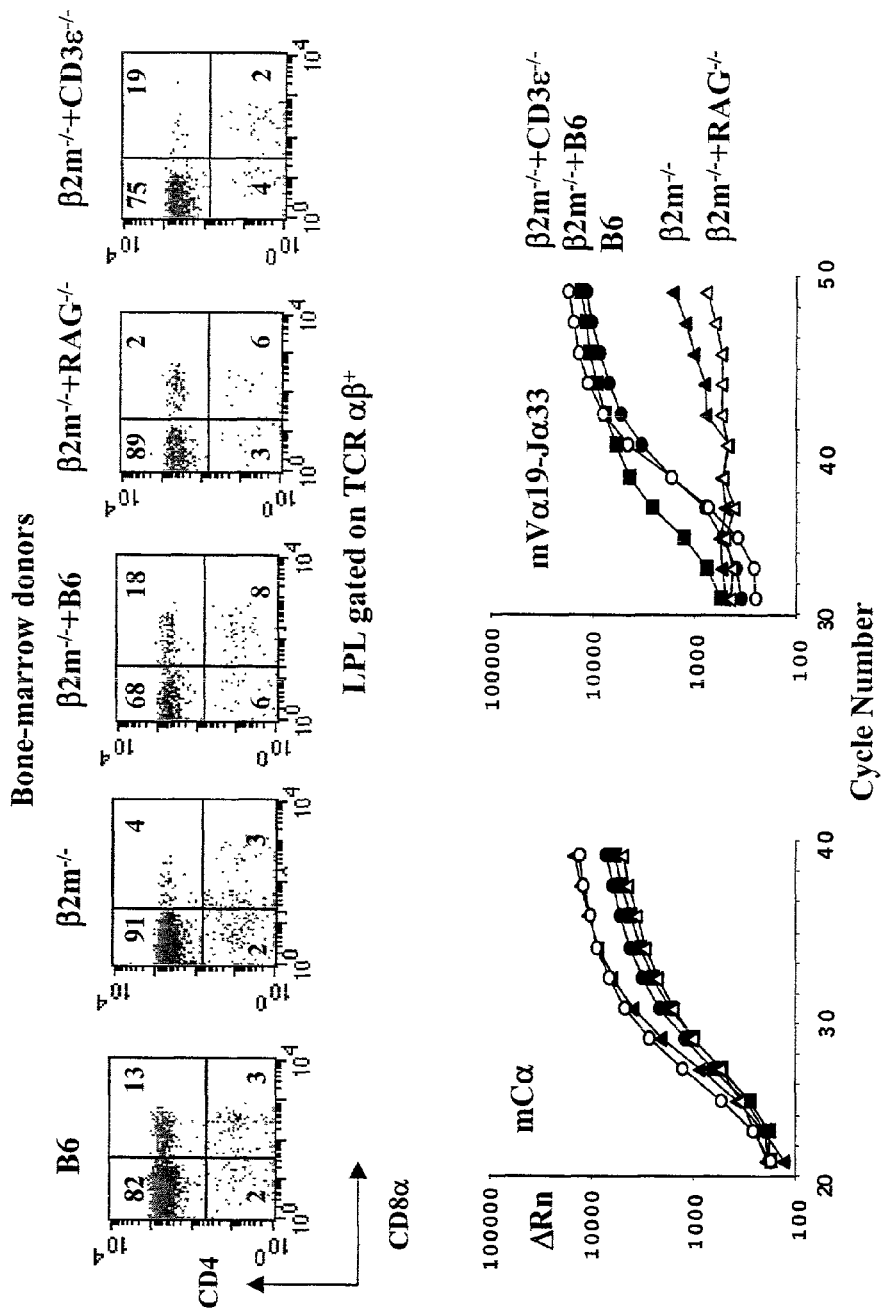
Fig. 3B The Vα19+ LPL are dependent upon the expression of their ligand on B cells Differential expression of the MR1 isoforms in different mouse tissues Phenotype of LPL in Vα19-Jα33 Tg mouse IgA levels in the feces of control and over-expressing Tg MAIT cell mice aKO = Cα-/-
DKO= TAP-/-Ii-/-
TKO= Cα-/-TAP-/-Ii-/-

Serum IgA levels in control and over-expressing Tg MAIT cell mice aKO = Cα-/-
DKO= TAP-/-Ii-/-
TKO= Cα-/-TAP-/-Ii-/-

Intracellular detection of IFN-γ production by MLN from B6 and Vα19 Tg mice after in vitro stimulation with PMA+Ionomycine in the presence of Monensin.

High IFNγ mRNA expression in Vα19 Tg mesenteric LN cells after anti-CD3 + anti-CD28 stimulation Membrane expression of mMR1A in Hom2 and RBL transfected with mMR1A-GFP.

Absence of mVα19-Jα33 transcripts in DN TCR αβ+ T cells isolated from the MLN of MRI KO mice.

T CELL SUBPOPULATION REGULATING GUT IMMUNITY

The invention relates to methods of modulating an immune response in a mammal by modulating the activity of Vα7.2/19-Jα33 TCR α chain bearing T cells in vitro, ex vivo or in vivo. The invention also relates to methods of regulating the activity of immune cells, particularly of T lymphocytes and/or B lymphocytes by regulating the activity of MR1 in vitro, ex vivo or in vivo. The invention also deals with a pharmaceutical composition comprising Vα7.2/19-Jα33 TCR α chain bearing T cells or a compound that modulates the activity of Vα7.2/19-Jα33 TCR α chain bearing T cells and a pharmaceutically acceptable vehicle or carrier. The invention further comprises methods of screening active compounds using MR1 or fragments thereof, or nucleic acid encoding the same, or recombinant host cells expressing said polypeptide. The invention further deals with methods of diagnosis for intestinal diseases related to a defect of the activity of said Vα7.2/19-Jα33 TCR α chain bearing T cells.

Mucosas are the largest contact area between the body and the outside. One of the main methods of defense against the gut pathogens is the secretion of high quantities of IgA in the intestinal fluids. There are high numbers of IgA secreting cells (ISA) in both Peyer's Patches (PP) and Intestinal Lamina Propria (LP) which depend upon the presence of a microbial flora (they are absent from germ-free mice) and are for a large proportion T dependent. The gut associated T cells comprise the intra-epithelial lymphocytes (IEL), the PP and LP lymphocytes. IEL express both γδ and αβ TCR (T Cell Receptor) and among the latter most are CD8αβ whereas the former are mostly CD8αα or DN (Double Negative). LP lymphocytes express mostly αβ TCR, which display a CD44+ memory phenotype and are commonly thought as deriving from naive T cells primed within the PP by gut antigens and recirculating before localizing in the LP. The repertoire analysis of gut lymphocytes has mostly focused on the TCRβ chains and have shown oligoclonal expansions which were not recurrent from one mouse to another indicating that they were probably antigen driven.

B and T lymphocytes display a wide repertoire of antigen receptors, made by random recombination of V, (D) and J segments and trimming/addition of nucleotides at the junctions between these rearranged segments. Two T lymphocyte subsets displaying repertoire with limited diversity and conserved between species have been described: the NK-T cells using mostly Vα14-Jα18 (but also Vα3.2-Jα9 and Vα8) in mice and the homologous segments Vα24-Jα18 in humans (Bendelac A et al. 1997. Annu. Rev. Immunol. 15:535-62) and the subset that we call hereinafter the Mucosal Associated Invariant T cells (MAIT cells) for the reasons we shall see, which uses Vα7.2-Jα33 in humans and the homologous segments Vα19-Jα33 in mice and cattle (Tilloy et al., J. Exp. Med., 1999, 1907-1921). Even if the function(s) of the NK T cells is not yet fully appreciated a great wealth of data has been accumulated and NK T cells have been implicated in immune class regulation, auto-immunity and anti-tumor immunity. Much less is known about the MAIT cells although the strict conservation of the specificity between species suggests an important role.

Both populations share common characteristics but also seem to be complementary with regards to tissue location and species abundance. They display a CDR3 of constant length paired with a limited number of Vβ segments together with an activated phenotype (CD44) and they seem to be the result of oligoclonal expansions (Lantz and Bendelac. 1994. J. Exp Med. 180:1097-106; Tilloy et al., J. Exp. Med., 1999, 1907-1921). They are CD4+ or CD4−/CD8− (DN) or CD8αα in humans and they do not seem to require the CD4 or CD8 accessory molecules to be selected. Both populations require the expression of their selecting element on hematopoietic derived cells and not on thymic epithelium contrary to mainstream αβTCR T cells (Bendelac A, 1995. J Exp Med. 182: 2091-6 and see below). They are both restricted by class Ib molecules (not classical, β2microglobulin (β2m) dependent but TAP independent) which is CD1 for NK-T. NK T cells are abundant in the thymus, liver, spleen and bone-marrow but quasi absent from peripheral lymph-nodes (PLN) and the gut associated lymphoid tractus (GALT).

The inventors have now discovered that the selecting class Ib molecule is MR1 for the Vα7.2-Jα33 human cells and for the Vα19-Jα33 cells in mice and cattle and that said mucosal associated invariant T (MAIT) cells are absent from the thymus, liver, spleen and bone marrow but are abundant in the gut lamina-propria (LP) and the mesenteric lymph nodes (MLN).

MR1 molecules are encoded by the MHC class I-related gene. The genomics, isoforms, expression and phylogeny of the MHC Class I-related MR1 gene are described by Hashimoto et al (Science 269 (1995) 693) and by Patricia Riegert et al. (The Journal of Immunology, 1998, 4066-4077). MR1 is expressed in many tissues but display many alternative spliced forms both in humans and in mice.

It has also been discovered that NK T cells are abundant in mice but not so in humans whereas MAIT cells are in high number in humans but much less numerous in mice.

Moreover, it has been established by the inventors that this Vα7.2/19-Jα33 TCR α chain bearing T cell subpopulation, which is conserved between species, is located in the gut lamina propria (LP) and in other mucosal tissues, such as in the lungs, and requires B cell for their accumulation. Transgenic over-expression of these cells induces the activation of LP B cell associated with higher levels of IgA in the intestinal fluids. The inventors have discovered that the most abundant spliced form of MR1 expressed in the gut is the full length one: MR1A. This finding probably explain the location of the Vα7.2/19-Jα33 TCR α chain bearing T cells. The said Vα7.2/19-Jα33 TCR α chain bearing T cells also seem involved in the regulation of lamina propria B cell functions through the recognition of the non-classical MHC class I molecule MR1 (by the secretion of lymphokines such as IFN-γ and TGFβ1). Thus, it can be established that these mucosa associated invariant T cells (MAIT cells) regulate the mucosal immunity.

In view of the above, an object of this invention is a method of modulating an immune response in a subject, in particular a mammal and more specifically in a human being, comprising administering to the subject a compound that modulates the activity of Vα7.2/19-Jα33 TCR α chain bearing T cells.

A further object of the invention resides in a method of regulating the activity of immune cells, particularly of T cells and/or B cells, by regulating the activity of Vα7.2/19-Jα33 TCR α chain bearing T cells.

The invention also relates to methods of screening compounds comprising determining the ability of a test compound to regulate the activity of Vα7.2/19-Jα33 TCR a chain bearing T cells, in particular by using MR1 or fragments thereof, or nucleic acid encoding the same, or recombinant host cells expressing said polypeptide.

The invention also relates to methods of screening compounds comprising determining the ability of a test compound to regulate the activity of Vα7.2/19-Jα33 TCR α chain bearing T cells or of MR1 polypeptide, in particular by binding to MR1 or fragments thereof, or nucleic acid encoding the same, or recombinant host cells expressing said polypeptide.

A further aspect of the invention is a pharmaceutical composition comprising a compound that modulates the activity of Vα7.2/19-Jα33 TCR α chain bearing T cells or of MR1 polypeptide and a pharmaceutically acceptable vehicle or carrier.

The invention also relates to methods of diagnosing a dysfunction in a subject, preferably a mammal, comprising determining the presence of a defect of the activity or of the number (increase or decrease) of Vα7.2/19-Jα33 TCR α chain bearing T cells or the presence of a mutation or alteration in a MR1 gene or RNA, or determining the presence or amount of a MR1 polypeptide or a ligand binding to MR1. In particular, it relates to methods of diagnosing an intestinal dysfunction in a subject.

For reason of simplicity, Vα7.2-Jα33 TCR α chain bearing T cells and Vα19-Jα33 TCR α chain bearing T cells are called hereinafter Jα33 T cells.

The invention is particularly suited to treat or diagnose pathologies in which the activity of immune cells is involved, particularly T cells and/or B cells. The invention is particularly suited to treat or diagnose pathologies in which the activity of T cells is involved such as viral infections, tumor or other proliferative diseases, autoimmune diseases, etc, in particular related to a mucosal disease. The invention can be used, by way of example, to treat patients with Crohn disease, ulcerative colitis or other inflammatory intestinal diseases.

MR1 Polypeptide

Within the context of this application, the term MR1 polypeptide designates preferably a mammalian MR1 polypeptide, even more preferably a human or rodent MR1 polypeptide. A preferred MR1 polypeptide of this invention comprises all or part of SEQ ID n°:1 identified in Genbank as ID n° U22963 or a functional derivative thereof.

SEQ ID n°:1 is as follows:

MGELMAFLLPLIIVLMVKHSDSRTHSLRYFRLGVSDPIHGVPEFISVGYV

DSHPITTYDSVTRQKEPRAPWMAENLAPDHWERYTQLLRGWQQMFKVELK

RLQRHYNHSGSHTYQRMIGCELLEDGSTTGFLQYAYDGQDFLIFNKDTLS

WLAVDNVAHTIKQAWEANQHELLYQKNWLEEECIAWLKRFLEYGKDTLQR

TEPPLVRVNRKETFPGVTALFCKAHGFYPPEIYMTWMKNGEEIVQEIDYG

DILPSGDGTYQAWASIELDPQSSNLYSCHVEHCGVHMVLQVPQESETIPL

VMKAVSGSIVLVIVLAGVGVLVWRRRPREQNGAIYLPTPDR

Fragments or parts thereof means any portion of at least 5 consecutive amino acids, typically from 5 to 100. Preferred fragments contain functional domains, such as ligand binding site. Functional derivatives include naturally-occurring variants, e.g., polymorphisms, splicing forms, homologs from other species, etc. It includes also synthetic derivatives, i.e., artificially created MR1 polypeptides having modified amino acid sequence as compared to SEQ ID n°:1 (U22963). Modification of amino acid sequence includes any mutation, deletion, or addition thereof. Functional derivative means that MR1 polypeptide retains the ability to bind Jα33 T cells or a specific receptor thereof or to bind a ligand of MR1.

The MR1 polypeptide of this invention is preferably in isolated or purified form (i.e., not in their natural environment). It may also be attached or immobilized to solid supports, such as columns, beads, etc. It may be combined to other active molecules or adjuvants or solvents. The MR1 polypeptide may be expressed from recombinant host cells. The MR1 polypeptide can be any polypeptide or fragment thereof encoded by the MHC class I-related gene. More preferably, the MR1 polypeptide is selected in the group consisting of hMR1-A, -B, -C and -D or mMR1-A, -B, -C, -D, -E, and -F, as described in Riegert et al., the Journal of Immunology, 1998, 4066-4077. The preferred MR1 polypeptide corresponds to the sequence SEQ ID n°:2. The MR1 polypeptide of this invention may be attached to any heterologous sequence or moiety, such as stabilizing agent, a marker, a tag, a targeting moiety, a drug, a cytokine, a toxin, etc.

The MR1 polypeptide can be used to produce antibodies, or multimers thereof, modulate an immune response, regulate the activity of Jα33 T cells in vitro, ex vivo or in vivo, screen for compounds that modulate Jα33 T cells activity, etc.

MR1 gene

The MR1 gene of this invention means any nucleic acid encoding a MR1 polypeptide as defined above. It includes any DNA (e.g., gDNA, cDNA, etc.) or RNA sequence. In a more preferred embodiment, the MR1 nucleic acid sequence corresponds to a sequence encoding the MR1 sequence SEQ ID n°:1 or a functional derivative thereof.

Vectors

The MR1 gene can be comprised in any vector. The vector may be any plasmid, phage, episome, artificial chromosome, virus, etc. Typical examples include plasmid vectors, such as those derived from commercially available plasmids (pUC, pBR322, pcDNA, etc.). Other preferred vectors are viruses, particularly recombinant (replication-defective) viruses, such as those derived from retroviruses, baculoviruses, lentiviruses, AAVs, adenoviruses, herpesviruses, etc. The vectors can be prepared by conventional techniques, e.g., by ligating the MR1 nucleic acid molecule into appropriate cloning site of the vector. The vector may further comprise regulatory sequences, such as promoters, terminators, enhancers, silencers, etc., origin(s) of replication, marker genes, etc. Typical examples of promoters include promoters allowing constitutive or regulated or tissue-selective expression, weak or strong promoters, of cellular, viral or synthetic origin, such as RVS-LTR, SV40-IE, CMV-IE promoter, promoters of domestic genes (PGK, etc.), promoters of bacteria or phage (T7, Lac, Trp, etc.), etc.

The vectors can be used to express a nucleic acid of this invention in vitro, ex vivo or in vivo. In particular, the vectors can be used to produce a MR1 polypeptide in a cell, in vitro or ex vivo, as well as directly in vivo, in a gene therapy program.

Host Cells

The present invention also relates to host cells comprising a nucleic acid molecule or a vector encoding the MR1 polypeptides as defined above. The polypeptide may be expressed within the cell cytoplasm or released from the cells by any means. The polypeptide may, in particular, be expressed as a soluble or secreted molecule.

The recombinant cell can be any cultivable cell, such as prokaryotic or eukaryotic cells, including bacteria, yeasts, insect cells, plant cells, mammalian cells, etc. The cell may be a cell line or a primary culture. Typical examples include *E. coli*, Saccharomyces, Kluyveromyces, insect cells, mammalian fibroblasts or embryonic cells, HEK, CHO, COS, 3T3, 293, etc. It should be understood that the invention shall not be limited to any specific type of host cell.

In a preferred embodiment, the host cell is a cell that does not naturally express a human or murine MR1 polypeptide. Such host cell can be used advantageously in screening assays, with increased selectivity.

Another object of this invention is a method of preparing cells expressing a MR1 polypeptide, said method comprising introducing into cells in vitro a nucleic acid molecule or a vector as defined above and selecting the cells or their progeny which express the polypeptide. Introduction of the nucleic acid or vector may be accomplished by various known means, such as by direct DNA transfer, lipid-mediated transfection, calcium-phosphate precipitation, electroporation, etc. The cells may be cultured in any suitable media and stored under any conventional methods.

Antibodies

The present invention also relates to an antibody that binds to a MR1 polypeptide or a Jα33 T cell as defined above. The antibody is preferably an antibody obtained by immunizing an animal with a polypeptide as defined above, with a host cell as defined above or a Jα33 T cell. In this regard, an object of this invention also includes a method of preparing an antibody, said method comprising injecting to a non-human mammal a polypeptide or a Jα33 T cell as defined above and collecting the antibody, serum or antibody-producing cells in said mammal.

The antibody may be a polyclonal or a monoclonal antibody as well as fragments and derivatives thereof, in particular fragments and derivatives of said antibodies having substantially the same antigenic specificity. These include antibody fragments (e.g., Fab, Fab'2, CDRs, etc), humanized antibodies, poly-functional antibodies, Single Chain antibodies (ScFv), etc. These may be produced according to conventional methods, including immunization of an animal and collection of serum (polyclonal) or spleen cells (to produce hybridomas by fusion with appropriate cell lines).

Methods of producing monoclonal antibodies from various species including mice, rodents, primates, horses, pigs, rabbits, poultry, etc. may be found, for instance, in Harlow et al (Antibodies: A laboratory Manual, CSH Press, 1988) or in Kohler et al (Nature 256 (1975) 495). Briefly, these methods comprise immunizing an animal with the antigen, followed by a recovery of spleen cells which are then fused with immortalized cells, such as myeloma cells. The resulting hybridomas produce the monoclonal antibodies and can be selected by limit dilutions to isolate individual clones.

Antibodies may also be produced by selection of combinatorial libraries of immunoglobulins, as disclosed for instance in Ward et al (Nature 341 (1989) 544).

Methods of producing polyclonal antibodies from various species, as listed above, may be found, for instance, in Vaitukaitis et al., 1971. Briefly, the antigen is combined with an adjuvant (e.g., Freund's adjuvant) and administered to an animal, typically by sub-cutaneous injection. Blood samples are collected and immunoglobulins or serum are separated.

Fab or F(ab')2 fragments may be produced by protease digestion, according to conventional techniques. Humanized antibodies can be prepared as described previously (Jones 1986).

Most preferred antibodies of this invention are functional antibodies, i.e., antibodies that regulate the activity of MR1, more particularly antibodies that can activate or block the interaction of MR1 with a Jα33 TCR cc chain bearing T cell. Such antibodies can be further selected by contacting an antibody as disclosed above with a Jα33 TCR α chain bearing T cell and a MR1 polypeptide, and by determining the ability of said antibody to block or to inactivate the Jα33 T cell. The present invention shows that such functional (e.g., blocking) antibodies can be produced and used to regulate the activity of immune cells.

The antibodies may be coupled to heterologous moieties, such as toxins, labels, drugs or other therapeutic agents, covalently or not, either directly or through the use of coupling agents or linkers. Labels include radiolabels, enzymes, fluorescent labels, magnetic particles and the like. Toxins include diphteria toxins, botulinum toxin, etc. Drugs or therapeutic agents include lymphokines, antibiotics, antisense, growth factors, etc. Methods of using such heterologous moieties are illustrated, for instance, in U.S. Pat. No. 4,277,149 and U.S. Pat. No. 3,996,345.

The antibodies of this invention have various applications, including therapeutic and diagnostic uses, and they may be used as well for immuno-purification or detection of a MR1 polypeptide or Jα33 T cells in a sample (e.g., plasma or serum samples), for instance. In particular, they can be used in vitro in screening assays as will be described below, or to detect or quantify the presence (or amounts) of MR1 polypeptide or Jα33 T cells in a sample collected from a subject, typically a blood sample from a mammalian, specifically a human subject.

Other Materials

Multimers, for instance tetramers or dimers, of MR1 or of TCR (Vα7.2-Jα33/Vβ13), immortalized cell lines expressing Jα33 TCR α chain, such as T-T hybridoma (for instance as described in Tilloy et al. JEM, 1999), or Vα19-Jα33 TCR transgenic mice that the inventors have obtained can be used to screen test compounds or to diagnose pathologies.

Screening

The present invention provides a method for screening compounds involved in the activity of Jα33 T cells and potentially of T and B cells, and in the regulation of the immune system. These compounds, as well as the corresponding nucleic acids, host cells, plasmids, and binding partners thereof, can be especially used in the area of immune regulation.

In particular, the invention relates to methods of screening compounds comprising determining the ability of a test compound to regulate the Jα33 T cells. Within the context of the present invention, the term "regulating Jα33 T cells" includes modulating the number of Jα33 T cells or expression thereof as well as modulating the biological activity of Jα33 T cells. When a compound activates Vα7.2/19-Jα33 TCR α chain bearing T cells, said compound preferably stimulates said cells to undertake activities related to generating a cell-mediated or immune response such as secreting a lymphokine.

Regulating the activity of Jα33 T cells thus includes the regulation of the number and expression thereof (over- or sub-expression) as well as the biological activity of Jα33 T cells (e.g., B cells interactions therewith, activation of LP B cells, activation of IgA secreting cells, level of Ig A, IFNγ or TGFβ production).

In an other embodiment, the invention relates to methods of screening compounds comprising determining the ability of a test compound to regulate the activity of MR1 polypeptide.

Within the context of the present invention, the term "regulating the activity of MR1 polypeptide" includes modulating the synthesis of MR1 polypeptide, the expression thereof, in particular the membrane expression thereof, as well as modulating the biological activity of the MR1 polypeptide. When a compound activates the MR1 polypeptide, said compound preferably stimulates the binding of MR1 polypeptide to said Jα33 T cells to undertake activities related to generating a cell-mediated or immune response, such as secreting a lymphokine.

Regulating the activity of MR1 polypeptide thus includes the regulation of MR1 synthesis or expression thereof (e.g., transcription, translation, trafficking, export, post-translational modification, etc.) as well as the biological activity of MR1 (e.g., its interaction with the said MAIT cells, the association of MR1 with another cellular partner, etc.)

Preferred compounds to be identified are those that selectively regulate the activity of Jα33 T cells or of MR1 polypeptide, i.e., that essentially do not directly interfere with another cell type or a restriction element different from MR1, although secondary effects may be induced.

In a particular embodiment, the method comprises determining the ability of a test compound to:
- bind to Jα33 T cells,
- bind to MR1 polypeptide,
- activate Jα33 T cells,
- inhibit Jα33 T cells,
- inhibit MR1 synthesis or (membrane) expression thereof,
- stimulate MR1 synthesis or (membrane) expression thereof,
- modulate MR1 binding to specific TCR of Jα33 T cells,
- modulate (e.g., block or activate) the interaction of said Jα33 T cells with MR1,
- modulate (e.g., block or increase) the activation of B-cells induced by MR1-selected T cell, In a particular embodiment, this invention lies in a method of selecting, screening or characterizing a compound, said method comprising contacting a test compound with Jα33 T cells as defined above or specific TCR thereof and determining the ability of said test compound to bind to said cells or TCR.

This method includes contacting a test compound with a specific TCR of Jα33 T cells.

Specific TCR of Jα33 T cells includes isolated functional receptors of Jα33 T cells that bind to MR1 polypeptide.

In a specific embodiment, the method further comprises contacting said test compound with at least another T cell type (e.g., T helper cell type, cytotoxic T lymphocytes, NK T cells) and determining the ability of said test compound to regulate (bind to) said other T cells as to identify selective compounds as defined above.

In another embodiment, the method comprises contacting said test compound with MR1 polypeptide or a fragment thereof, or nucleic acid encoding the same, or recombinant host cells expressing said polypeptide and determining the ability of said test compound to bind to said MR1 polypeptide or to said fragment thereof.

This particular embodiment allows the identification of compounds that bind to MR1 and potentially modulate the biological activity of Jα33 T cells.

The invention thus also relates to a method of selecting, screening or characterizing a compound, said method comprising contacting a test compound with Jα33 T cells or specific TCR thereof as defined above in the presence of a MR1 polypeptide or a fragment thereof, or nucleic acid encoding the same, or recombinant host cells expressing said polypeptide as defined above (said host cell expressing a MR1 polypeptide), and determining the ability of said test compound to compete with or to increase the binding of said MR1 to said cells.

The contacting step according to the invention is preferably carried out in the presence of B cells, precursors thereof, or cells secreting IgA, more particularly in the presence of LP B cells.

The ability of a test compound to bind to TCR or to MR1 may be determined by various techniques known in the art. In vitro, the binding may be determined by electrophoresis, SPA, FRET, etc. or by competition with a labelled MR1 polypeptide. In this regard, in a preferred embodiment, binding is determined by measuring the ability of the test compound to modulate the binding of a labelled MR1 polypeptide.

According to another embodiment of the invention, the MR1 polypeptide, Jα33 T cells or specific TCR thereof can be replaced by an antibody anti-MR1 polypeptide or anti-TCR Jα33 T cells (Vα7.2-Jα33/Vβ13), eventually labelled, as described above, a multimer, for instance tetramer or dimer, of MR1 or of TCR (Vα7.2-Jα33/Vβ13), immortalized cell lines expressing Jα33 TCR α chain, such as T-T hybridoma, for instance as described in Tilloy et al., or Vα19-Jα33 TCR transgenic mice that the inventors have made.

The invention also relates to a method of selecting, screening or characterizing a compound, said method comprising contacting a test compound with Jα33 T cells as defined above (or specific TCR thereof), optionally in the presence of MR1 polypeptide or a host cell as defined above (said host cell expressing a MR1 polypeptide), and determining the ability of said test compound to decrease or to increase a biological response induced by MR1 polypeptide.

In a particular embodiment, the process is carried out in the presence of B cells, precursors thereof or cells secreting IgA.

The biological response may be, for instance, activation of LP B cell, an increase of the expressed levels of Ig, a cytolytic activity, an increase of IFN-γ or TGFβ secretion, etc. In particular, the biological response can be the production of IgA, IFN-γ or TGFβ.

In a particular embodiment, the invention comprises contacting a test compound with Jα33 T cells (or specific TCR thereof) in the presence of an antibody specific for MR1 and determining the activity of said test compound by measuring the biological activity of said T cells (or the binding to said specific TCR).

In a further embodiment, the invention relates to a method of selecting, screening or characterizing a compound comprising contacting a test compound with Jα33 TCR T cells in the presence of a MR1 polypeptide and assessing the capacity of said test compound to modulate the interaction between said MR1 polypeptide and said Jα33 T cells. The screening of compounds having the ability to interfere with said interaction thus provides molecules having the ability to regulate the activity of MR1 or of Jα33 T cells.

Such a screening can be performed in vitro, by contacting a MR1 polypeptide (or a host cell expressing a MR1 polypeptide) with the test compound and the said T cells.

In a particular embodiment, a screening method comprises (i) determining the ability of a test compound to bind to Jα33 T cells and (ii) determining the ability of a test compound selected in (i) to regulate (e.g., block, reduce or stimulate) one of the functions of B cells (e.g., the proliferation of B cells or the secreting IgA, TGFβ or IFNγ activity thereof).

The test compound may be any synthetic compound, including organic products, lipids, peptides, proteins, nucleic acids (e.g., antisense), etc. The assay may be performed in any suitable device, such as plates, tubes, dishes, flasks, etc. Typically, the assay is performed in multi-wells plates. Several test compounds can be assayed in parallel. Furthermore, the test compound may be of various origin, nature and composition. It may be any organic or inorganic substance, isolated or in mixture with other substances. The compounds may be all or part of a combinatorial library of products, for instance.

Modulation of Immune Response

The invention provides a method of modulating an immune response in a subject, in particular a mammal, comprising administering to the subject in need of such modulation a compound that modulates the activity of Jα33 T cells or MR1 polypeptide.

A further object of the invention resides in a method of regulating (in vivo, in vitro or ex vivo) the activity of immune cells, particularly of T cells and/or B cells, by regulating the activity of Jα33 T cells or MR1 polypeptide.

The Jα33 T cells or MR1 polypeptide are involved in the regulation of immune function, and their modulation or regulation can thus produce a regulation of an immune function in vivo, in particular in mucosal tissues and more particularly in digestive tissues. In particular, compounds that regulate the activity of MR1 may be used to regulate the activity of Jα33 T cells, and consequently B cells or other T cells, particularly to stimulate or inhibit the activity of Jα33 T cells, more specifically the Jα33 T cells-mediated B cells activation or inhibition and in particular activation or inhibition of LP B cells.

The compound that modulates the activity of Jα33 T cells or MR1 polypeptide includes any compound identified by the screening method as defined above. Said compound can also be selected in MR1 or fragments thereof, or nucleic acid encoding the same, recombinant host cells expressing said polypeptide as defined above, or a MR1 antibody as defined above. The Jα33 T cells, specific TCR, or antibodies thereof can also be used per se to regulate the activity of immune cells, particularly of T cells and/or B cells and more specifically to LP B cells or B cells of other mucosal tissues.

An object of this invention thus lies in a method of regulating an immune response in a subject comprising administering to the subject a compound that (selectively) regulates the activity of Jα33 T cells or of MR1 polypeptide. The invention also relates to the use of a compound that (selectively) regulates the activity of Jα33 T cells or of MR1 polypeptide in the manufacture of a medicament for regulating an immune response in a subject, and in particular a mucosal immune response.

The invention also relates to a pharmaceutical composition comprising Jα33 T cells, MR1 polypeptide, a host cell expressing MR1 polypeptide or the specific TCR of Jα33 T cells or a compound that regulates the activity of Jα33 T cells or of MR1 polypeptide, and a pharmaceutically acceptable vehicle or carrier. Particular compositions comprises a compound that stimulates the activity of Jα33 T cells or that inhibits the activity of Jα33 T cells.

A particular object of this invention thus resides in a composition that comprises Jα33 T cells or a compound that regulates the activity of Jα33 T cells and a compound that regulates the activity of another T cell type or B cells, for combined, sequential or separated use.

The compound is preferably a compound that activates (or inhibits) Jα33 T cells, particularly a MR1 polypeptide as defined above (or an anti-MR1), or a molecule selected or identified by a method as described above.

The compounds may be administered according to various routes, enterally or parenterally, such as by per os, intravenous, intra-arterial, intramuscular, intra-dermic, intra-peritoneal, etc. The compounds may be used in various dosages that can be adapted by the skilled person.

The compounds are particularly suited to stimulate an immune response in a human subject, particularly to stimulate Jα33 T cells in a human subject. Such compounds are also suitable for use in the treatment, prevention or diagnosis of pathologies in which the activity of Jα33 T cells is involved, such as viral infections, tumor or other proliferative diseases, autoimmune diseases, etc, in particular related to a mucosal disease. The invention can be used, by way of example, to treat patients with Crohn disease, ulcerative colitis or other inflammatory intestinal diseases.

The invention also relates to methods of diagnosing a dysfunction in a subject, comprising determining, for instance in a sample derived from said subject, the presence of a defect of the activity of Jα33 T cells or the presence of a mutation or alteration in a MR1 gene or RNA, or determining the presence or amount of a MR1 polypeptide.

These methods may be performed using antibodies, tetramers or dimers or nucleic acid primers or probes as described above to numerate or isolate the Jα33 bearing T cells or MR1 expressing cells. For instance, quantitative PCR on purified on blood samples can be carried out to seek for an absence of Jα33 bearing T cells as described below in the Btk deficient patients. One can also isolate the Jα33 T cells to measure their lymphokine producing capacity either by ELISA, by intracellular staining or by ELISspots. The method can be performed with any sample derived from a subject, such as tissue samples, in particular mucosal tissue sample, such as gut tissue, colon tissue, or serum, blood, plasma, other biological fluids, etc.

These methods of diagnosing is particularly suited to diagnose for intestinal diseases (or a risk of developing the same) related to a defect of the activity of said Jα33 T cells or of MR1 polypeptide.

Further aspects and advantages of the present invention will be disclosed in the following examples, which should be regarded as illustrative and not limiting the scope of this applications. All cited references are incorporated therein by reference.

LEGEND TO THE FIGURES

Figure 1B:
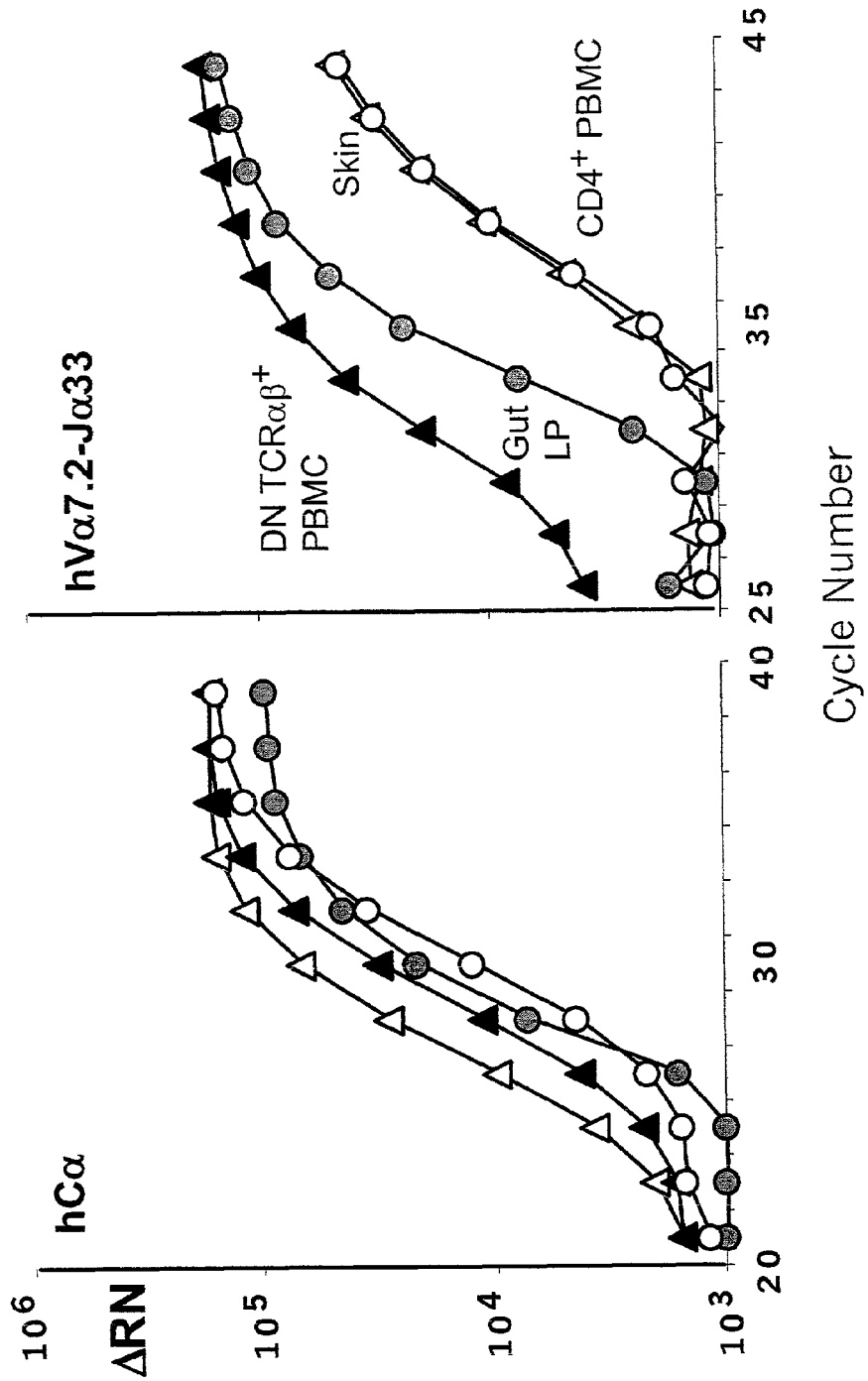
Figure 1C:
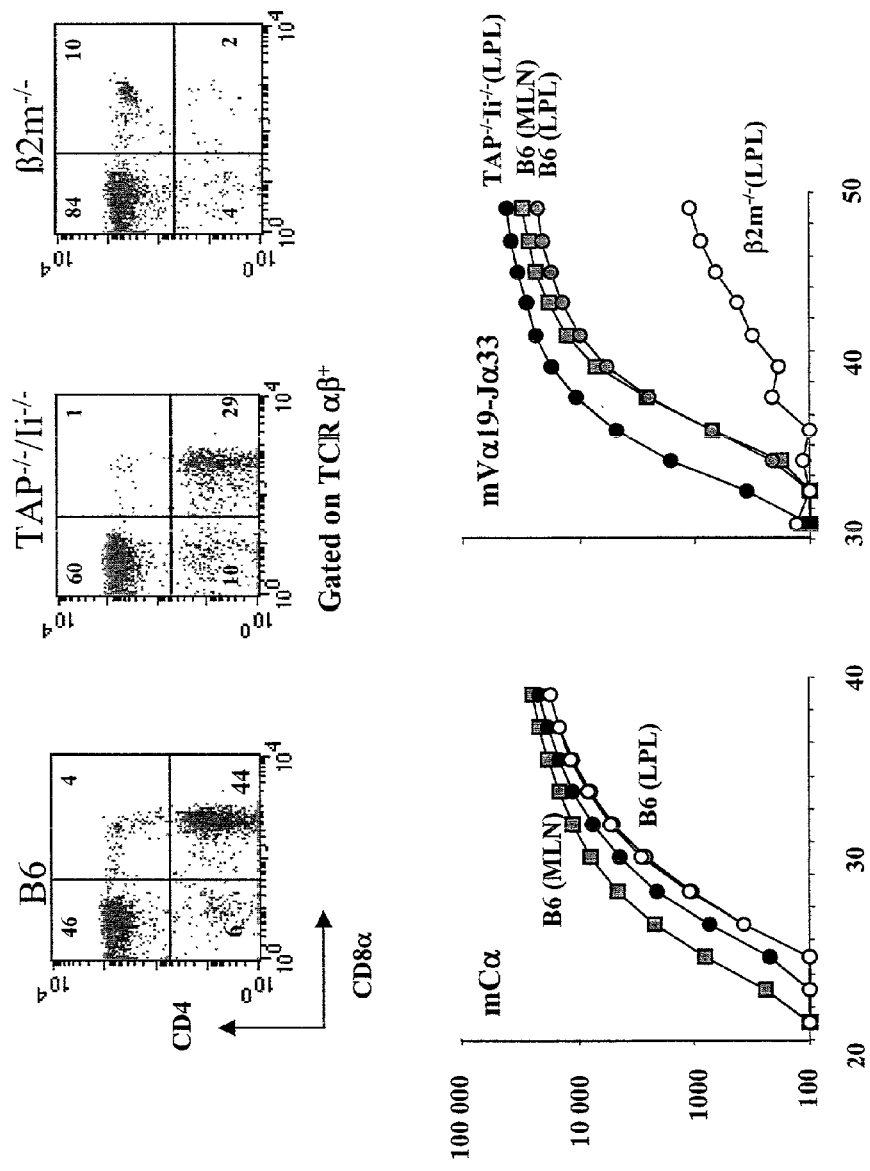
Figure 1:
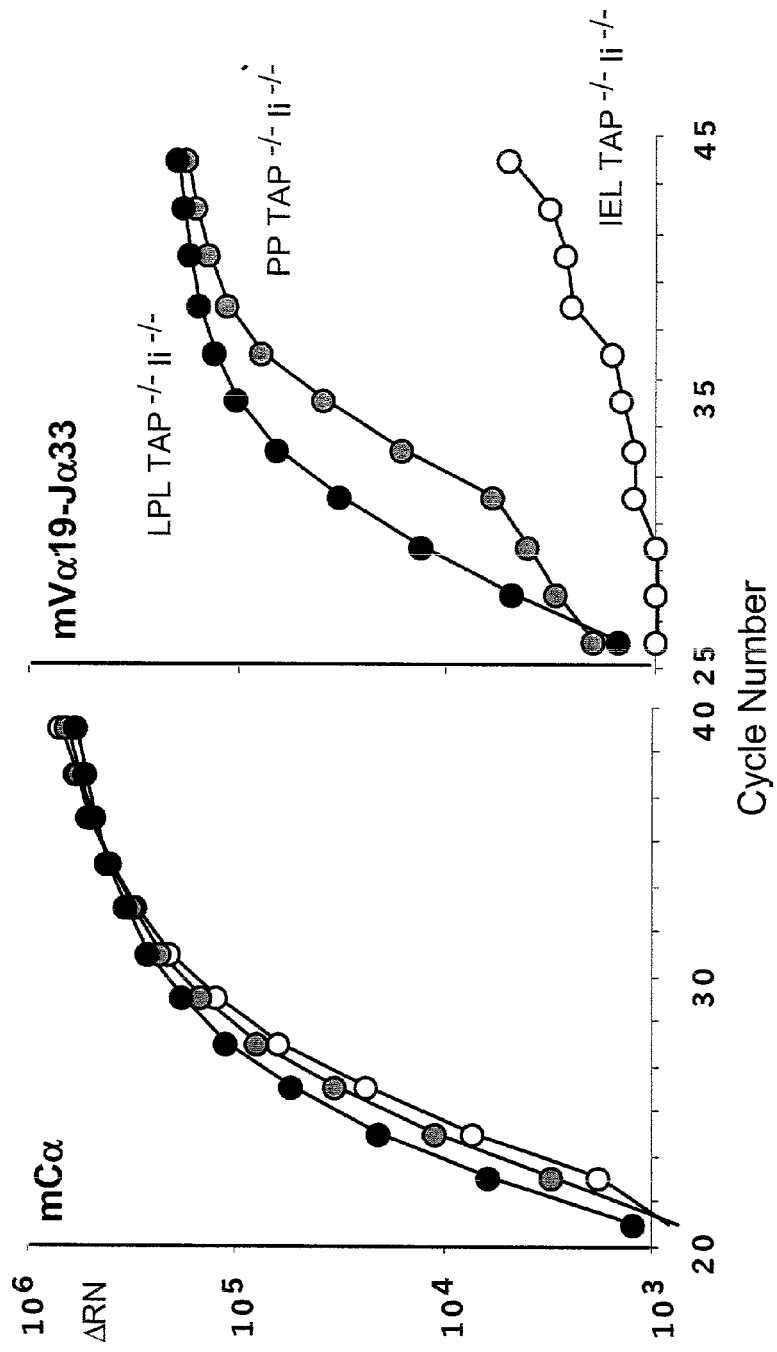

FIG. 1. A Human invariant Vα7.2-Jα33 bearing cells express the gut homing marker FIG. 1. B Human invariant Vα7.2-Jα33 bearing cells are present in the gut LP and PP and not in the skin FIG. 1. C Mouse Vα19-Jα33 bearing cells are present in the gut LP and MLN FIG. 1. D Mouse Vα19-Jα33 bearing cells are present in the gut LP and PP and not in IEL FIG. 2. A Cellularity of the different organs of Vα19-Jα33 TG mice FIG. 2. B Increased usage of the Vβ8 segments in Vα19-Jα33 TG mice FIG. 2. C Increased usage of the Vβ6 and Vβ8 segments in Vα19-Jα33 TG mice FIG. 3. A Selection of Vα19-Jα33$^+$ T cells requires the expression of their ligand on hematopoietic derived cells FIG. 3. B Vα19+ LPL are dependant upon the expression of their ligand on B cells FIG. 3. C Decreased number of mVα19-Jα33$^+$ LPL and hVα7.2-Jα33$^+$ PBL in the absence of B cells FIG. 3. D Presence of Vα19-Jα33$^+$ LPL in mMT$^{-/-}$ mice FIG. 3. E MAIT cells are absent from Germ-free mice FIG. 4. A MR1A spliced form is preferentially expressed in the Lamina propria FIG. 4. B LP B cells are activated and express more IgA in mice over-expressing MAIT cells FIG. 4. C LP B cells are activated and express more IgA in mice over-expressing MAIT cells FIG. 5. A IgA levels in the feces of mVα19-Jα33 Tg Mice FIG. 5. B IgA levels in the serum of mVα19-Jα33 Tg Mice FIG. 5. C Sub-normal Ig in the serum of mice over-expressing MAIT cells FIG. 5. D Increased expression of IFN-γ in LPL from mVα19-Jα33 Tg Mice FIG. 5. E Quantitation of TGFβ in mitogen stimulated MLN DN lymphocytes from mice over-expressing MAIT cells FIG. 5. F Quantitation of IFN-γ mRNA in anti-CD3+anti-CD28 stimulated MLN lymphocytes from mice over-expressing MAIT cells FIG. 6. A Expression of mMR1A-GFP on RBL and HOM2 transfectants FIG. 6. B Membrane expression of mMR1A-GFP on RBL and HOM2 transfectants FIG. 6. C Vα19-Jα33 T-T hybridoma respond to MR1A transfectants FIG. 6. D Vα19-Jα33 Tg MLN T cells respond to MR1A transfectants FIG. 7. A Strategy for inactivating MR1 (From S. Gilfillan and S. Barham)

FIG. 7. B Phenotype of T and B cells in the spleen of MR1 deficient mice

FIG. 7. C MAIT cells are absent in MRI deficient mice

MATERIALS AND METHODS

Mice $β2m^{-/-}$ and Cu deficient mice (both N9 to C57B1/6 (B6)) and CD45.1 congenic B6 were obtained from the CDTA central animal CNRS animal facility (Orléans, France). TAP deficient mice were obtained from the Jackson laboratory on a B6/129 background. Ii (B6/129) and μMT (N10 to B6) deficient mice were obtained from the CDTA. $Cα^{-/-}$, Ii and TAP deficient mice were intercrossed to get double or triple deficient mice. Common interleukin receptor gamma chain (γc) deficient mice were obtained from J. Disanto, and crossed to $RAG2^{-/-}$ and $β2 m^{-/-}$ mice to obtain triple deficient mice as described (I. Grandjean, in preparation). Xid and $J_H$ deficient mice were kindly given by P. A. Cazenave's team (Institut Pasteur). Germ free mice (C3H) and matched controls were purchased from the CDTA.

Vα19-Jα33 transgenic mice were obtained as described (Tilloy et al., J Exp Med., 1999; 189(12):1907-21) by cloning a PCR product obtained from DN T cell cDNA into the TCR alpha shuttle vector (Patten). The construct was injected into B6/DBA2 F1 eggs at the CNRS transgenic facility (I. Cerruti, Villejuif, France). Five founder lines were backcrossed for at least 9 generations to Ca deficient mice. Three of the lines were also backcrossed to Ca-/-/TAP-/-/Ii-/- for at least 9 generations and are therefore in a mixed B6/129 background (the $H-2^d$ MHC haplotype has been eliminated by screening at the beginning of the breeding program). All mice were housed in our conventional SPF colony and genotyped by PCR.

Cell Preparation

Cell suspensions were prepared from thymus, spleen, peripheral or mesenteric lymph nodes by gentle mechanical disruption through a nylon mesh in PBS supplemented with 0.5% BSA. Gut Lamina propria lymphocytes were prepared as described elsewhere (Guy-grand et al, J. Exp. Med.): briefly, the gut was flushed several times with PBS to eliminate intestinal content, and after peyer's patches removal, the intestine was opened longitudinally and washed again in cold PBS. The epithelium was eliminated by incubating 5 cm pieces twice in 60 ml of PBS+3 mM EDTA for 10 min, then twice in 15 ml of CO2-independant medium containing 1% dialysed FCS, 1 mM EGTA and 1.5 mM MgCl2 for 15 min, at 37% under shaking. The gut pieces were vortexed for 2 min, cut in 0.5 cm pieces and stirred for 90 min at 37° C. in 30 ml of CO2-independant medium supplemented with 20% FCS, 100 U/ml collagenase and 5 U/ml DNase I. At the middle and at the end of the incubation, the suspension was flushed several times through a syringe to increase dissociation. The pellet was washed, filtered through a 22 μm cell strainer and the LPL were separated by centrifugation over a lympholyte M gradient.

Flow Cytometry

Flow cytometry was performed as described in Tilloy et al. (J. Exp. Med., 1999, 1907-1921), using the following antibodies: CD4-APC, CD8α-FITC, TCR αβ-cy, CD69-PE, CD44-PE, Vβ6-PE, Vβ8-PE, H2-Kb PE, B220-cy, IgA-FITC, CD80-PE, Mac1-APC (Pharmingen). Acquisitions were performed on a FACScalibur® (BD). For intracellular staining, after cell surface staining, the cells were fixed with Facs Lysing buffer (BD), incubated 30 min in 40 μl of Saponin+Milk, then 10 μl of anti IgA-FITC, IFN APC or IL4 PE diluted in saponin+milk were added. After 30 min, cells were washed in PBS +saponin and resuspended in PBS-BSA. For intracellalr cytokine detection, cells were first stimulated 2h30 with PMA and Ionomycine in the presence of monensin. We used a combination of a CD4-PE, CD8α-APC and TCR αβ-FITC, for cell sorting on a FACSvantage® (BD). All analysis were done using the CellQuest® software (BD).

Fetal Liver Chimeras

Twelve weeks-old C57B1/6 (CD45.2 or CD45.1) or b2 $m^{-/-}$ mice (CD45.2) were i.p. injected at day −1 and day 0 with 0.3 (D-1) and 0.4 mg (D0) of PK136 mAb; after the second injection, mice were sublethally irradiated (950 cGy), and 6 h later injected with 5 millions liver cells prepared from day 15 C57B1/6 (CD45.2 or CD45.1) or $β2m^{-/-}$ (CD45.2) foetuses. 3 months later, mice were killed and the thymus, lymph nodes and spleens were harvested. Phenotypic analysis was performed by flow cytometry as described, and the level of chimerism was appreciated by use of the congenic CD45.2/1 markers. The real-time RT-PCR and the polyclonal sequencing were performed on TCR $αβ^+$ DN-enriched fractions from lymph nodes. Briefly, lymph nodes cells were stained with anti-CD4 FITC and anti-CD8-FITC magnetic beads, washed twice and incubated with anti-FITC beads. The cells were then passed through a MS column on a MACS® magnet (Myilteny), and the effluent was collected as negative (CD4-CD8-) fraction. For each group of mice, the frequency of DN among TCR $αβ^+$ cells was above 80%, as checked by flow cytometry.

Bone Marrow Chimeras

Bone marrow cell suspensions from 12 weeks old C57/B16 and P2 m−/− mice were treated with anti-Thy1.2 ascite (kindly provided by Dr A. Lehuen) and complement in the presence of 10 μg/ml of DNase I (Sigma) for 1 h at 37° C. to eliminate mature T cells. $5. 10^6$ β2m−/− BM cells together with 5.106 C57/B16, $RAG2^{-/-}$ or $CD3ε^{-/-}$ BM cells were injected i.v. into RAG2-/-gc-/-b2m-/- hosts which had been treated 2 days before with x mg/ml 5 F.U. As controls, 107 b2m-/- or C57/B16 BM cells were injected in RAG2-/-gc-/-b2m-/- hosts. 3 months later, mice were killed, and the thymus, spleen, mesenteric lymph nodes were harvested. LPL were also extracted from the small intestine as described. Cell suspensions from all these organs were stained with a panel of mAbs to study the chimerism and the hematopoietic reconstitution.

Cloning of mMR1A cDNA from total C57B1/6 PBMC or human B cells was amplified for 35 cycles with the following primers:

```
                                                    SEQ ID n°:2
5'mouse aagaaggagatctgtgatggtgctcctgttacctctgctcg.

SEQ ID n°:3
3'mouse agagaaagaattcgagagggagagcttccctcattcacttg;

SEQ ID n°:4
5'human aaaaaatttccgctagcgggatgggggaactgatggcgttc,

SEQ ID n°:5
3'human tttttaaccctcgagtcgatctggtgttggaaggtagatgg.
```

The PCR product was loaded on a 0.8% LMP agarose gel, and after migration, the upper 1 Kb band was excised and purified using minelute gel extraction Kit (Qiagen). The purified product was then cloned in the EGFP-N1 vector (Clontech).

Transfections

The mMR1A in EGFP-N1 product was linearized by digestion with ApaLI, ethanol precipitated and the pellet was dissolved in sterile TE buffer at 1 µg/µl. $10^7$ RBL or Hom2 cells were washed twice in cold PBS, resuspended in 800 µl DMEM, and incubated 10 min with 20 µg of digested mMR1A-EFGPN1. Cells were then electroporated in 4 mm-cuves (Biorad), and after 10 min incubation, resuspended in complete RPMI medium and plated in 6-wells plates at $2.10^5$ cells/ml. After 24 h, G418 was added at 1 mg/ml (RBL) or 0.5 mg/ml (Hom2). After 10-14 days, positive wells were tested for GFP expression by FACS analysis, and the GFP+ cells were sorted for GFPhi expression with a FACSvantage®. RBL or HOM2 GFPhi transfectants were then plated at 1 cell/well, and after 10-14 days, the clones were tested for GFPhi expression.

Membrane Biotinylation and Immunoprecipitation $10^7$ cells were incubated with 0.5 mg/ml of biotin in 1 ml of cold PBS for 7 min, diluted with 10 ml of cold PBS and centrifugated for 7 min at 4° C. (1200 rpm). The pellet was then resuspended in 3 ml of cold PBS+Glycin 0.1M, incubated 10 min on ice, diluted with 10 ml cold PBS, centrifugated 3 min at 4° C. (3000 rpm) and resuspended in lysis buffer (0.5% Triton, 300 mM NaCl, 50 mM Tris, pH 7.4, and 10 µg/ml leupeptin, chemostatin, aprotinin, pepstatin, and N-ethyl maleimide).

For immunoprecipitation, the cells were incubated 30 min on ice and centrifugated 15 min at 14000 rpm at 4° C. 50 µl of Streptavidin-agarose beads were washed in lysis buffer+antiproteases, and added to 50 µl of the cell lysis supernatant, incubated for 6 h on a rolling wheel at 4° C., washed 3 times in lysis buffer+antiproteases, centifugated for 1 min at 14 000 rpm, and resuspended in 20 µl of loading dye.

Western Blot

Cells were lysed by incubation in lysis buffer as above. Cell lysates were diluted in reducing sample buffer and boiled for 5 min before electrophoresis in 8% polyacrylamide gels containing SDS. Proteins were electro-transferred to polyvinylidone fluoride membranes (Millipore). The membranes were incubated with blocking solution, followed by primary anti-GFP antibody and then horseradish peroxidase-labeled species-specific antibody. Chemiluminescence was detected with a Boehringer kit. Blots were visualized in a Storm 860 machine (Molecular Dynamics).

Elisa

For IgA detection in the mice feces, samples were <<dilacerated>> in 10% (v/w) TNC buffer containing 10 mM Tris pH 7.4, 140 mM NaCl, 10 mM CaCl2 and 0.05% Tween 20. Samples were vortexed, incubated 45 min on ice, centrifugated for 5 min at 4° C. at 10000 rpm, and the supernatants were collected and kept at −80° C. until further analysis.

96-wells plated were coated 2 h at 37° C. with 200 µl of anti-IgG1 (0.7 µg/ml), IgG2a (7 µg/ml), IgG2b (7 µg/ml), IgE(1/200), IgA (1 µg/ml) or TGFβ (0.5 µg/ml) capture antibodies, in a pH 9.6 NaHCo3 buffer. After 4 washes with PBS tween 0.05%, plates were saturated with PBS BSA 0.1% for 1 h at 37° C., and washed again 4 h with the same wash buffer. Serums or pretreated feces supernatant or culture supernatant) were added and incubated overnight at 4° C. Serial dilutions of each sample (except for TGFβ) ranging from 1/5000 to 1/500 000 (IgG1, 2a, 2b), or 1/100 to 1/10 000 (IgE) or (IgA) were tested. After 5 washes, Phosphatase Alkaline conjugated anti mouse IgG (1/1000) or IgA (1/1000) was added, and after 2 hours incubation at 20° C., the plates were washed 5 times, and incubated with Sapphire (1/50)+CDPStar (1/500) in 0.1 M Diethanolamine buffer. For IgE and TGFβ detection, biotinylated anti-IgE (1/3000) or anti-TGFβ (1 µg/ml) was used for 2 h at 37° C.; after 5 washes, PA-conjugated Streptavidin (1/2000) was added, and after 1 h incubation at 37° C. followed by 5 washes, the wells were incubated for 30 min at 20° C. with sapphire and CDPStar. The luminometric reaction was measured with a Victor apparatus (wallac).

IT-T Hybridoma and Screening Hematopoietic Cell Lines and Transfectants

T-T hybridoma were made as described (Tilloy et al, 1999) from DN T cells from mesenteric lymph nodes of TAP$^{-/-}$/Ii$^{-/-}$ mice. Among 356 growing wells, 58 were positive for the Vα19-Jα33 canonical sequence. As the Vα19-Jα33 starting frequency was around 2-5%, there is clearly a bias towards the fusion of Vα19-Jα33 positive cells, which might reflect their in vivo activation. 9 hybridoma were Vβ6 and 16 were Vβ8 confirming the results obtained with another batch previously published hem). Cell lines or stable transfectants to be screened were irradiated and distributed at 5 $10^4$ cells per well in flat bottomed 96 well plate and 5 $10^4$ hybridoma were added. After a 48 h incubation, the supernatant was harvested and tested for IL-2 content with the IL-2 dependent CTLL2 cell line.

Location of Vα7.2/19-Jα33$^+$ T cells. We have previously showed that T cells bearing the invariant Vα19-Jα33 TCR α chain are undetectable in all lymphoid organs but lymph nodes and that they display a memory phenotype (Tilloy et al., J. Exp. Med., 1999, 1907-1921). As some invariant antigen receptor bearing cells are located in specific organs of the body such as the peritoneal cavity for B1 cells or skin or genital mucosa for some γδ sub-populations, we examined in more details the tissue location of Vα7.2/19-Jα33$^+$ T cells. We hypothesized that, blood Vα7.2/19-Jα33-bearing cells could be in fact coming from peripheral non-lymphoid tissues. To determine which tissue these cells were coming from, we FACS sorted TCR αβ$^+$ DN from human PBL according to the gut tissue-specific homing marker α4β7. Using real-time quantitative PCR (Q-PCR), the Vα7.2-Jα33 transcripts segregated in the TCR αβ$^+$ DN α4β7$^+$ fraction, indicating that Vα7.2-Jα33$^+$ T cells were associated with the gut (FIG. 1A). Indeed, Vα7.2-Jα33 transcripts were enriched in the gut lamina propria (FIG. 1B) and Peyer's Patches (not shown) and not in the IEL nor in the skin (FIG. 1B). To examine whether the mouse Vα19-Jα33 bearing T cells would also be located in the gut, we quantified the amount of the Vα19-Jα33 canonical chain by Q-PCR in different organs. Since these T cells are very few in mice, we increased their frequency by generating mice deficient in both TAP and Ii molecules. These mice harbor a higher proportion of Vα19-

Jα33+ T cells as the number of main-stream T lymphocytes is decreased because the classical selecting MHC molecule expression is greatly diminished. Lymphocytes were isolated from the gut Lamina Propria of B6, TAP$^{-/-}$Ii$^{-/-}$, and β2 m$^{-/-}$ mice and mVα19-Jα33 Q-PCR was carried out. As shown in FIG. 1C, while the amount of Cα was 10 fold lower in a B6 LP than in a MLN sample, both cDNAs gave rise to the same Vα19-Jα33 PCR curves indicating that the LP sample contains much more Vα19-Jα33 cells than MLN. Polyclonal sequencing of the amplified Vα19-Jα33 amplicons confirmed the over representation of the canonical CDR3 specific of this invariant TCR α chain (not shown). mVα19-Jα33 transcripts were also absent in the LP lymphocytes from β2 m$^{-/-}$ and were 10 fold more abundant in TAP$^{-/-}$Ii$^{-/-}$ compared to B6 LP lymphocytes (FIG. 1C) in accordance with our previous work studying lymph-nodes (em). Importantly, mVα19-Jα33 transcripts were also abundant in PP lymphocytes but absent in the IEL (FIG. 1D). These results demonstrate that the gut lamina propria is the preferential location of the class Ib restricted invariant Vα19-Jα33 bearing T cells. In addition, preliminary data both in humans and in mice showed that MAIT cells are also present in the lung (data not shown) suggesting that MAIT cells may not be restricted to the gut but present in several mucosal tissues. We will therefore name Vα7.2/19-Jα33 bearing T cells, Mucosal Associated Invariant T (MAIT) cells.

Figure 2B:
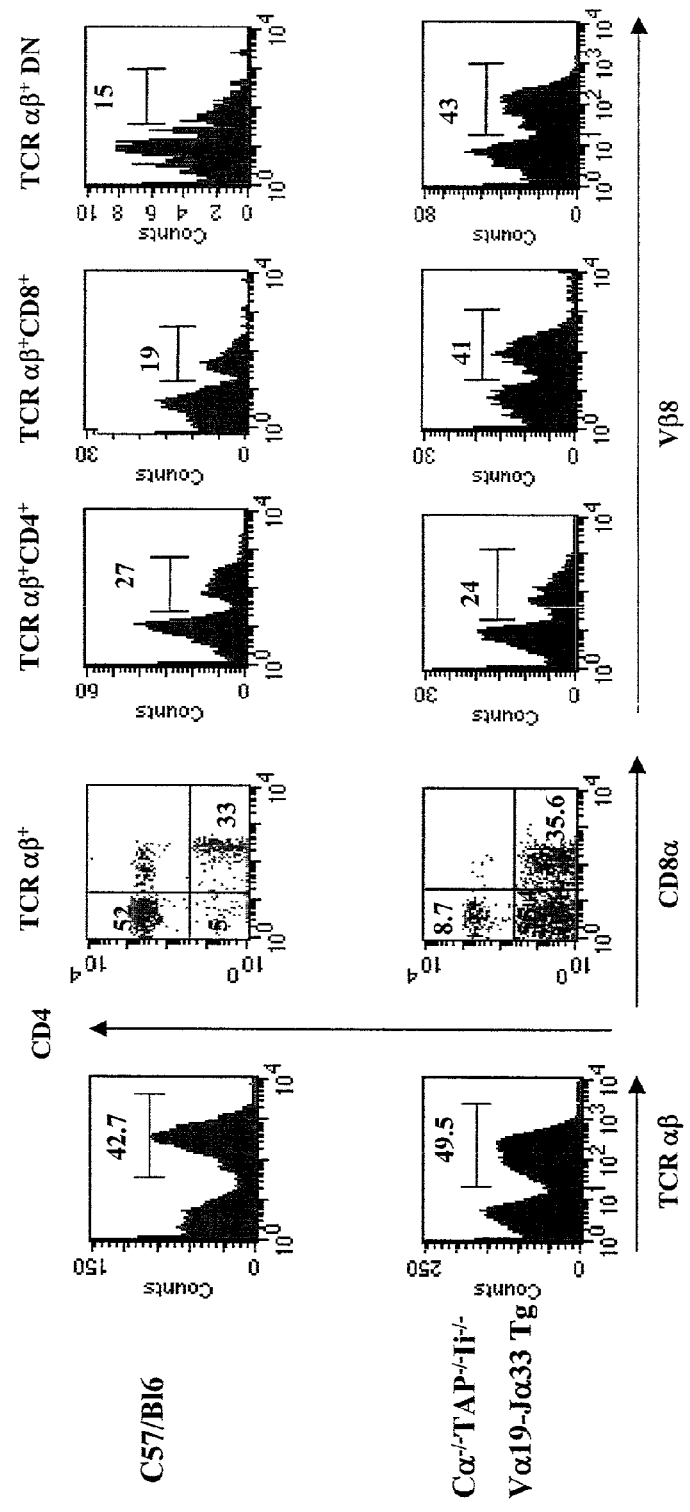
Figure 2C:
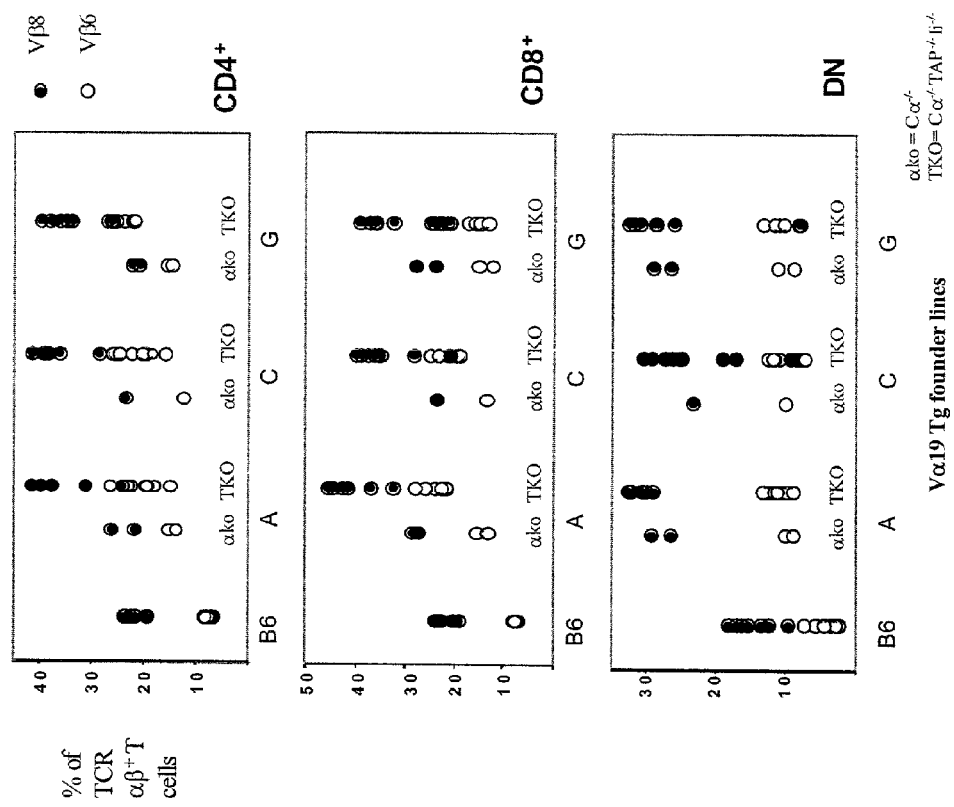

Vα19-Jα33 transgenic mice over-express the MAIT cells. In an attempt to increase the number of T cells expressing the Vα19-Jα33 specificity to better study this T cell population, we generated transgenic (Tg) mice for the invariant Vα9-Jα33 TCR α chain. Three different founder lines (A, C, G) were studied and were backcrossed onto a Cα$^{-/-}$ B6 background to avoid endogenous TCR α chains. In all the lines, the thymus contained very few mature thymocytes, and they were also very few TCR αβ+ lymphocytes in the peripheral LN, whereas MLN and especially LP displayed sub normal cellularity (FIG. 2A). The level of TCR β chain expression varied according to the founder but, in all cases the number of DN TCR αβ T cells was highly increased to 50% and the number of CD8+ T cells was 30-40% while CD4+ were reduced to 5-15% (FIG. 2B). In Cα$^{-/-}$ TCR α chain Tg mice, TCR β chain expression is not controlled and, even paired with the Tg TCR α chain, could give rise to a quite wide repertoire which could induce the selection of a large number of classical MHC class Ia or class II restricted T lymphocytes diluting the specific MAIT cells. To avoid these conventional T cells, the Vα19-Jα33 Tg founder lines were also crossed to a triple KO Cα$^{-/-}$/TAP$^{-/-}$/Ii$^{-/-}$ background. As shown in FIG. 2C, the T lymphocyte cellularity of these triple KO Tg mice were similar to that of Tg Cα$^{-/-}$ mice, except in the spleen where the T cell numbers were also decreased. The numbers of MLN and LP T cells were slightly increased when compared to Tg Cα$^{-/-}$ mice. These results are consistent with the absence of detectable mVα19-Jα33+ T cells in the thymus and spleen and their preferential location in the MLN and the LP of B6 or TAP$^{-/-}$Ii$^{-/-}$ mice. We have previously shown that Vα19-Jα33+ T-T hybridoma express preferentially Vβ8 and Vβ6 segments (JEM). To verify that the Vα19-Jα33 Tg MLN and LP lymphocytes were indeed representative of the MAIT cells, we studied their Vβ segment usage. As expected, the proportion of MLN lymphocytes from Vα19-Jα33 Tg mice using either Vβ6 and Vβ8 was largely increased in CD4+ and CD8+ subsets (FIG. 2D). In the gut, the situation was slightly different, as Vβ6 usage was strikingly increased in CD4+ LPL while CD8+ and DN LPL preferentially used Vβ8 (FIG. 2E). Thus, transgenic over-expression of the invariant Vα19-Jα33 chain is sufficient to induce the accumulation of Vβ6+ and Vβ8+ T cells in the gut, confirming that the gut lamina propria is a privileged site for Vα19-Jα33 bearing T cells.

Ontogeny of MAIT cells. Mainstream T cells are selected on classical MHC class I and class II molecules expressed on the thymus epithelium. On the other hand, the other invariant TCR α chain bearing T cell subpopulation, the NK-T cell, is selected/recruited by the recognition of CD1d expressed on hematopoietic-derived cells, the CD4+/CD8+ (DP) thymocytes. As we have previously shown that MAIT cells require a β2 m dependent molecule, in order to examine the selection process of MAIT cells, we generated fetal liver chimeras between β2 m deficient and wt B6 mice. The number of MAIT cells in the lymph node DN T cells of these different chimeras was estimated by measuring Vα19-Jα33 amounts by Q-PCR. As expected, B6→β2 m$^{-/-}$ (B6 fetal-liver transferred into irradiated β2 m deficient recipient) chimera have very few CD8+T cells, in agreement with the absolute requirement for MHC class I expression on the thymus epithelium to positively select the mainstream CD8+ T cells (FIG. 3A). mVα19-Jα33 transcripts were present in B6→β2 m$^{-/-}$ but not in β2 m$^{-/-}$→B6 chimeras as shown by Q-PCR (FIG. 3A). Polyclonal sequencing of the amplicons confirmed the abundance of the canonical sequence in the amplified Vα19-Jα33 amplicons (not shown). Thus, the expression of the putative β2m-dependent ligand on hematopoietic-derived cells is necessary and sufficient to allow accumulation of DN MAIT cells in the lymph-nodes. To identify what type of hematopoietic cell type was responsible for the selection of the MAIT cells, we generated mixed chimeras in which, the bone marrow from β2 m deficient mice (BM-#1) was mixed with a bone marrow of different origins (BM-#2) and then injected into β2 m deficient alymphoid hosts (β2 m$^{-/-}$/RAG2$^{-/-}$/γc$^{-/-}$). In this setting, the T cells derive from BM-#1 after repopulating the host thymus and are β2 m deficient while BM-#2 derived cells are the only source of β2 m. Therefore, when the BM-#2 is RAG2$^{-/-}$, only macrophage and dendritic cells display β2 m dependent MHC molecules whereas when BM-#2 is CD3ε$^{-/-}$, there are B cells in addition. In all the groups, very few CD8$^{hi}$ T cells were generated, as the host thymus epithelium does not harbor classical MHC class I molecule (FIG. 3B). As shown in FIG. 3B, when the source of the β2 m was the macrophages and the dendritic cells, no Vα19-Jα33 transcript could be found in the LPL whereas the addition of β2 m+ B cells was sufficient to give rise to Vα19-Jα33+LPL. These results indicate that T cells are dispensable for MAIT selection (contrary to NK T cells) whereas DCs or macrophages are not sufficient and suggest an important role for B cells.

Figures 3C, 3E:
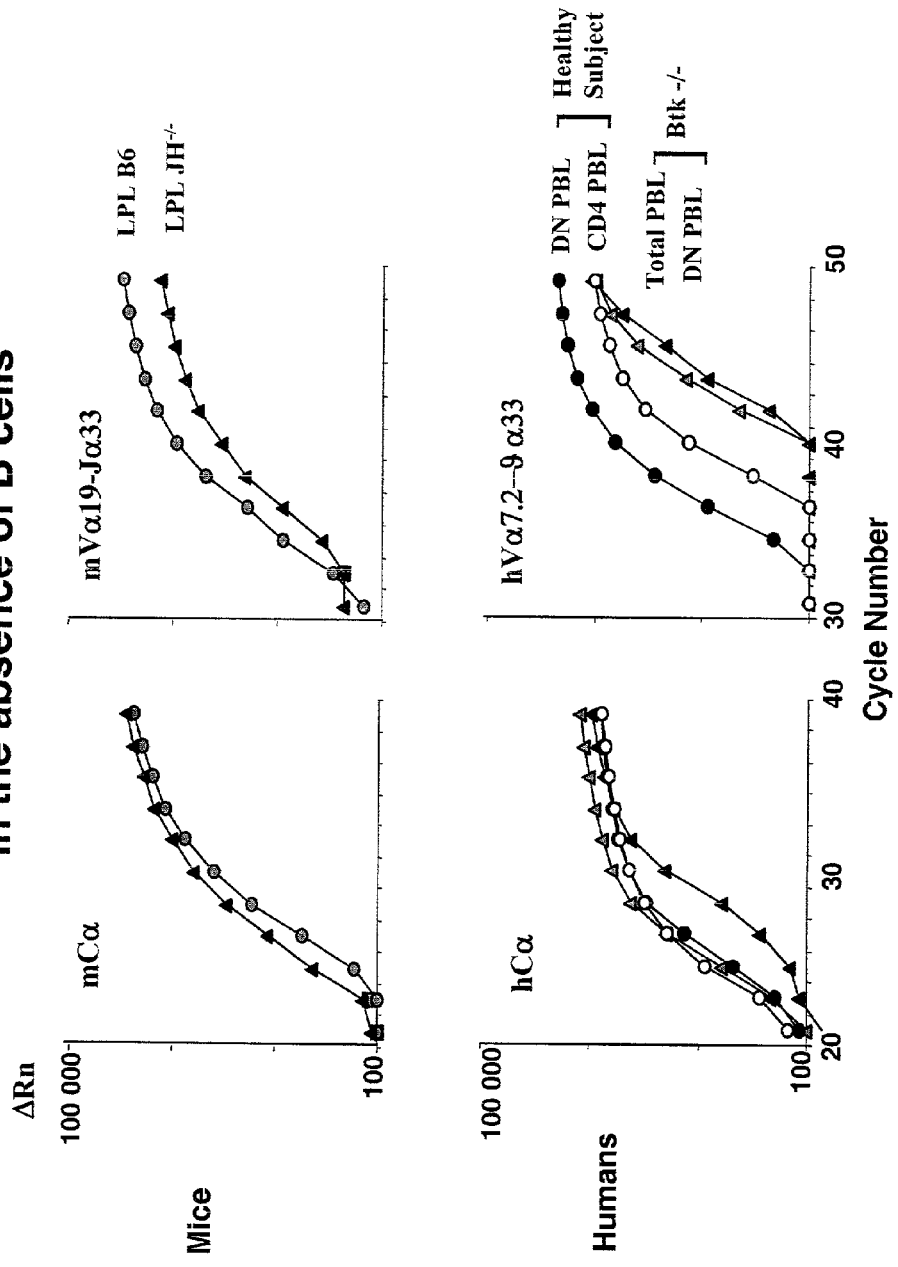
Figure 3D:
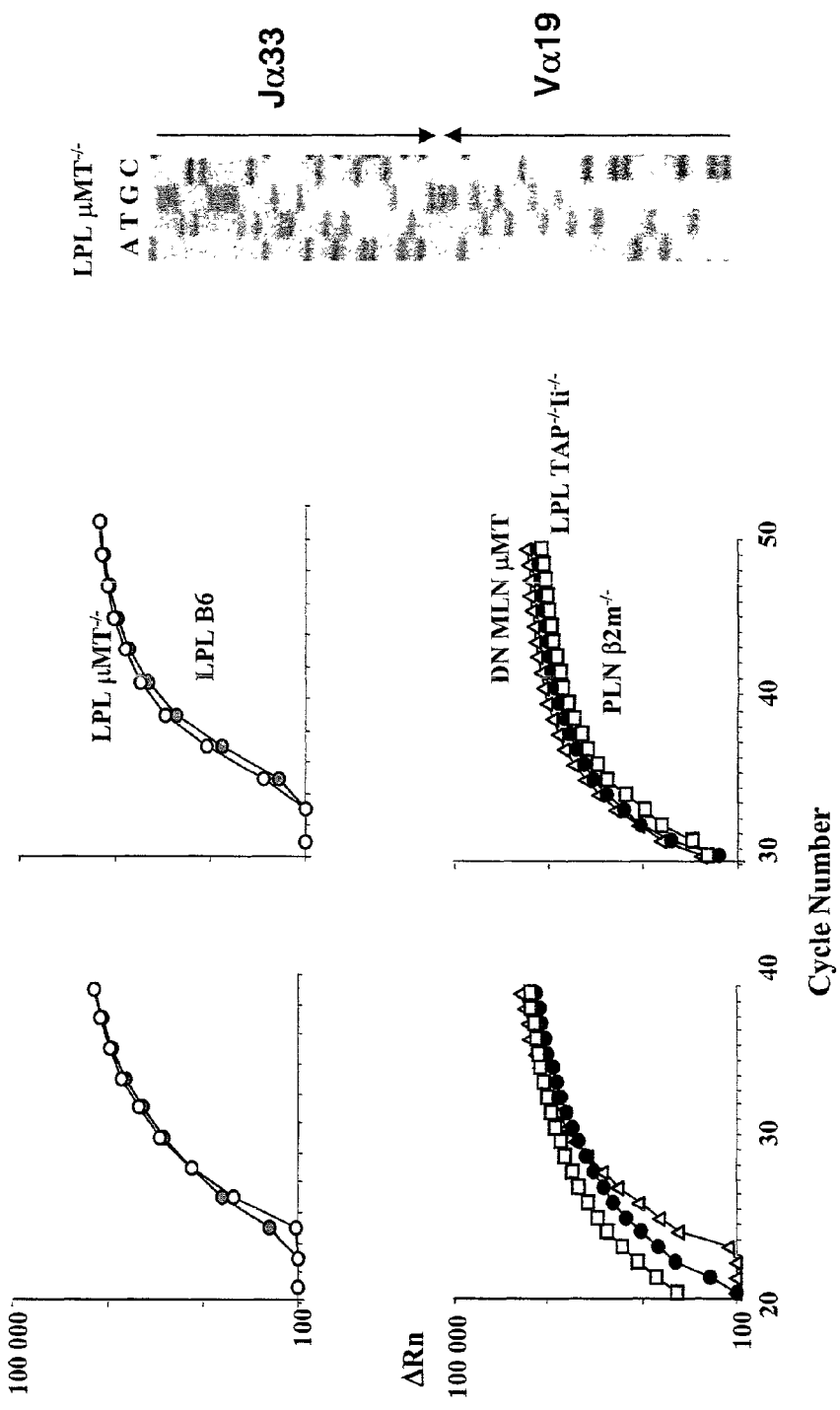

The selection of MAIT cells by B cells was further confirmed by the significant decrease in the amount of Vα19-Jα33 transcripts in the TCR αβ+ DN of MLN and in the LPL from J$_H$$^{-/-}$ mice, which are completely deficient in B cells (FIG. 3C). Polyclonal sequencing of the amplicons demonstrated that the canonical sequence was not present in J$_H$$^{-/-}$ mice, although Vα19 and Jα33 segments were used together with CDR3 of different lengths (FIG. 3D). To examine whether human MAIT cells would also require the presence of B cells, we quantified Vα7.2-Jα33 transcripts in the TCR αβ+ DN human PBL from a normal individual and from 2 patients deficient in the Bruton tyrosine kinase (Btk$^{mutated}$) who do not have B cells. As shown in FIG. 3E, the amount of hVα7.2-Jα33 transcripts in the DN T cells of these patients was very low compared with the normal subject. Altogether, these results show that B cells are necessary for the accumulation of MAIT cells in the MLN and the gut of B6 mice and in the peripheral blood of humans.

Recently, it was found that mice deficient in the transmembrane region of IgM (μMT$^{-/-}$) mice harbor IgA producing cells in their intestine despite an almost complete B cell deficiency. We therefore examined whether these B cells would be able to select the MAIT cells by measuring the amount of Vα19-Jα33 transcripts in the LPL of μMT$^{-/-}$ mice. As shown in FIG. 3F, a normal a normal number of MAIT cells was found in the LPL of B-cell deficient μMT$^{-/-}$ mice, indicating that gut B cells are sufficient for the selection of MAIT cells.

As MAIT cells are located in the gut lamina propria, an extra-thymic pathway of development could be hypothesized. However, even in the lamina-propria of old nude mice we were unable to find any canonical Vα19-Jα33 transcripts (not shown) confirming our previous report (Tilloy et al, 1999). Finally, we asked whether MAIT cell accumulation would be antigen driven by studying the lamina propria of germ-free mice. As shown in FIG. 3D, no canonical Vα19-Jα33 transcripts could be found in the lamina propria or the MLN DN T cells obtained from several germ-free mice. This result suggests that either MAIT cells recognize a conserved epitope derived from some common pathogen(s) or that an endogenous ligand is up-regulated by the commensal microbial flora.

Figure 4A:
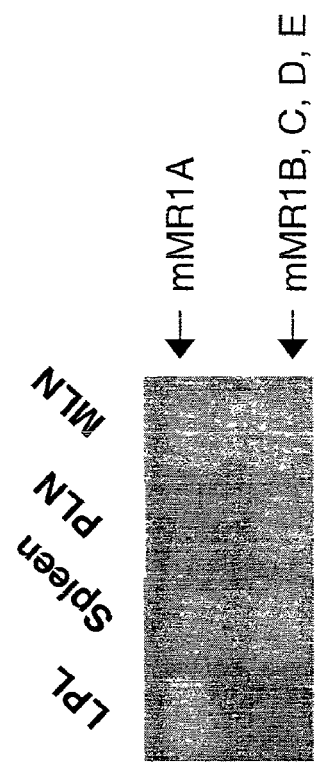
Figure 4B:
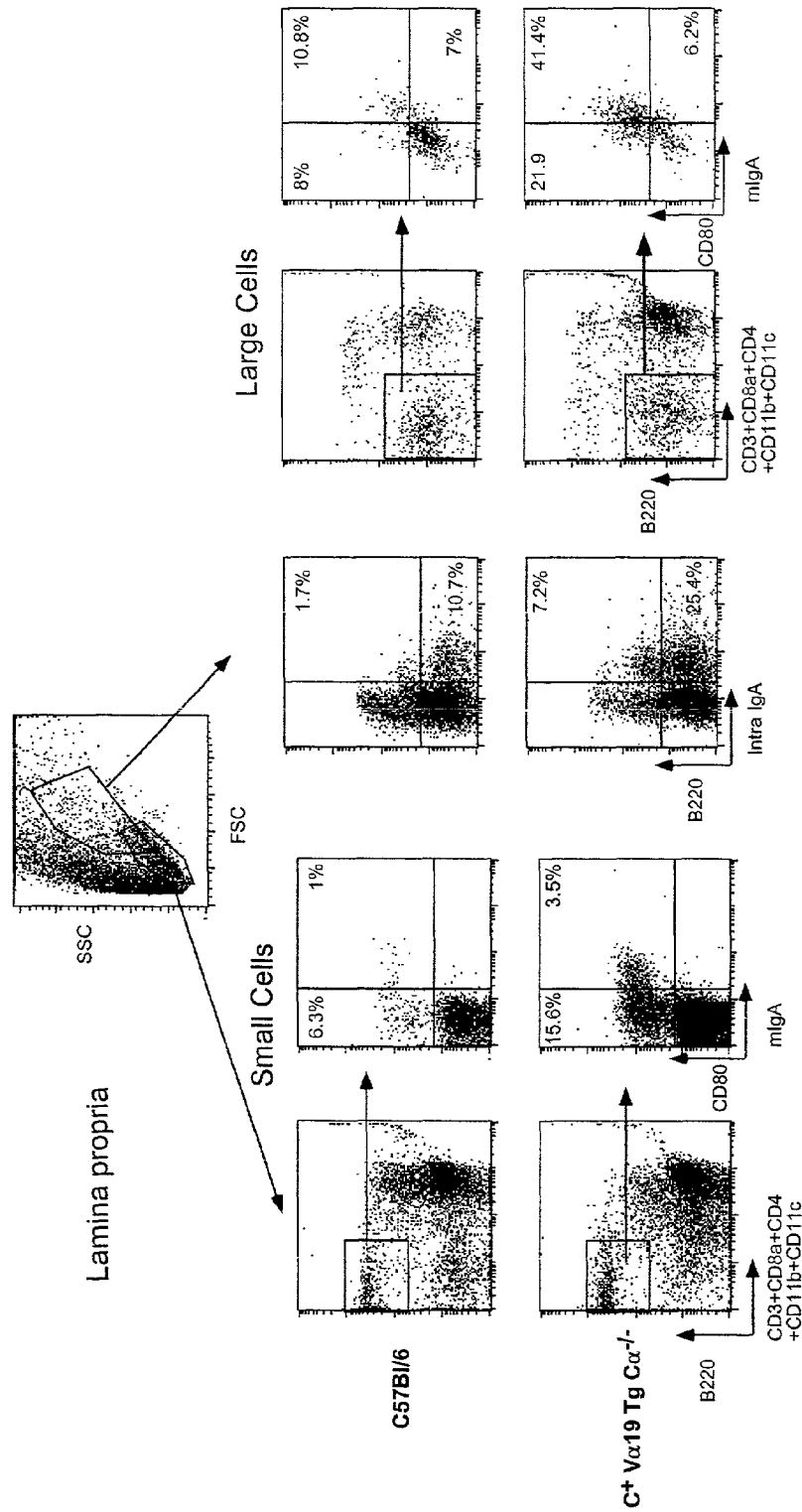
Figure 4C:
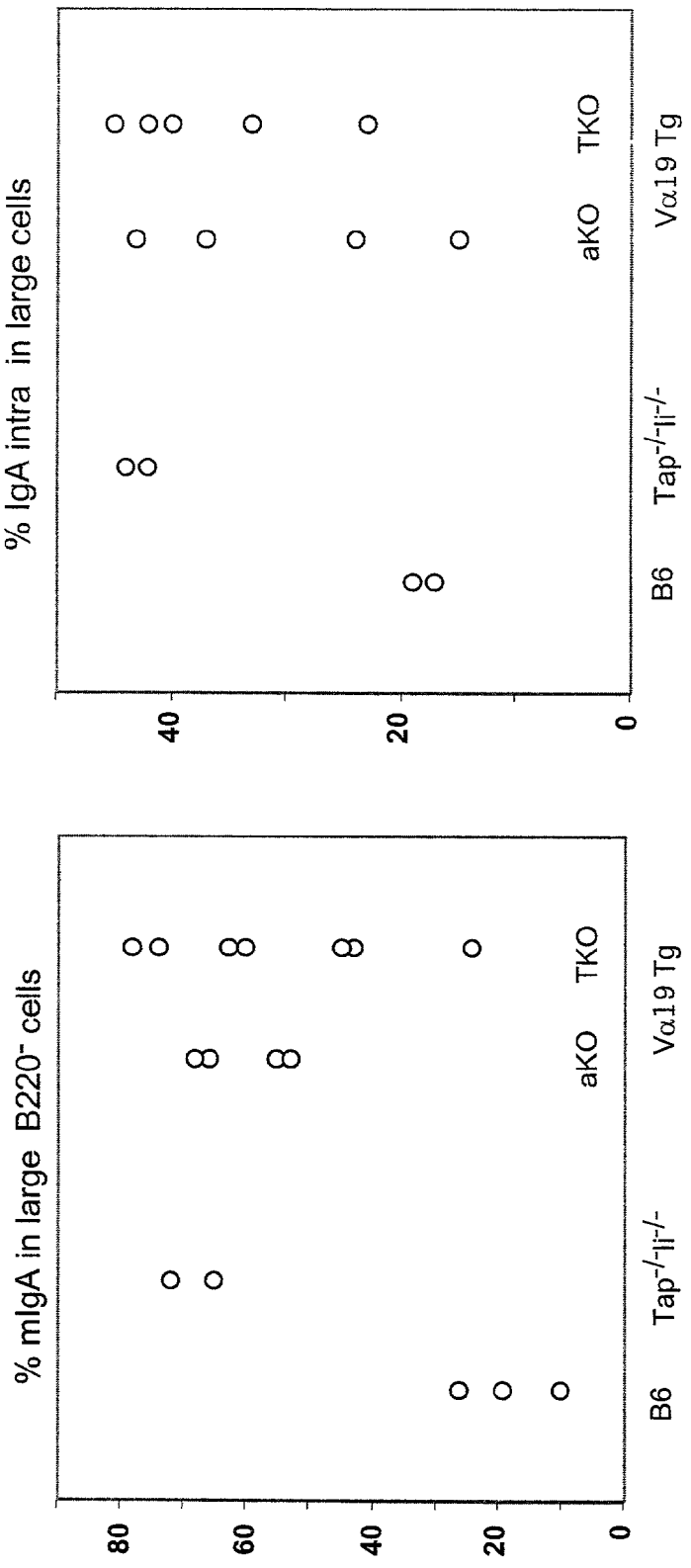

B cells and MAIT cells. In the companion paper, we demonstrate that MAIT cells are selected by the MHC class Ib molecule, MR1. MR1 is expressed in many tissues but display many alternative spliced forms both in humans and mice. Although there are no available anti-MR1 antibody, sequence analysis suggests that only the largest mRNA (coding for MR1A) allow the expression of a functional protein. To examine whether the gut location of MAIT cells would be related to the preferential expression of a functional MR1 protein, we PCR amplified MR1 with primers allowing to distinguish the different spliced forms on cDNA from spleen or LP B cells. As shown in FIG. 4A, the predominant spliced MR1 molecule was the largest one in LP B cells whereas the shortest ones were more abundant in the spleen suggesting that the location of MAIT cells in the LPL could be related to the expression of their ligand in this organ. Because there are no good markers, which can reliably distinguish activated B1 and B2 cells in the LP, we were unable to assess whether MRIA would be differentially expressed in these 2 cell populations. We next studied the number and the phenotype of B cells in Vα19-Jα33 Tg mice which over-express MAIT cells. As shown in FIG. 4B, the number of mature B cells (CD19$^+$/B220$^{hi}$/IgD$^{hi}$) was decreased in the LP while there was an increase in the proportion of activated B cells (B220$^{int}$/gD$^{int}$/) with a higher expression of CD80 in this subset. In contrast, all B cell subsets displayed a normal phenotype in the other lymphoid organs such as spleen and MLN (FIG. 4B). Furthermore, in the Tg mice LP, the number of big cells expressing surface IgA was increased when compared to control mice (FIG. 4C). Thus, over-expression of MAIT cells induces over-activation of B cells and increased number of IgA producing plasmocytes exclusively in the lamina propria.

Functions of MAIT Cells.

Figure 5A:
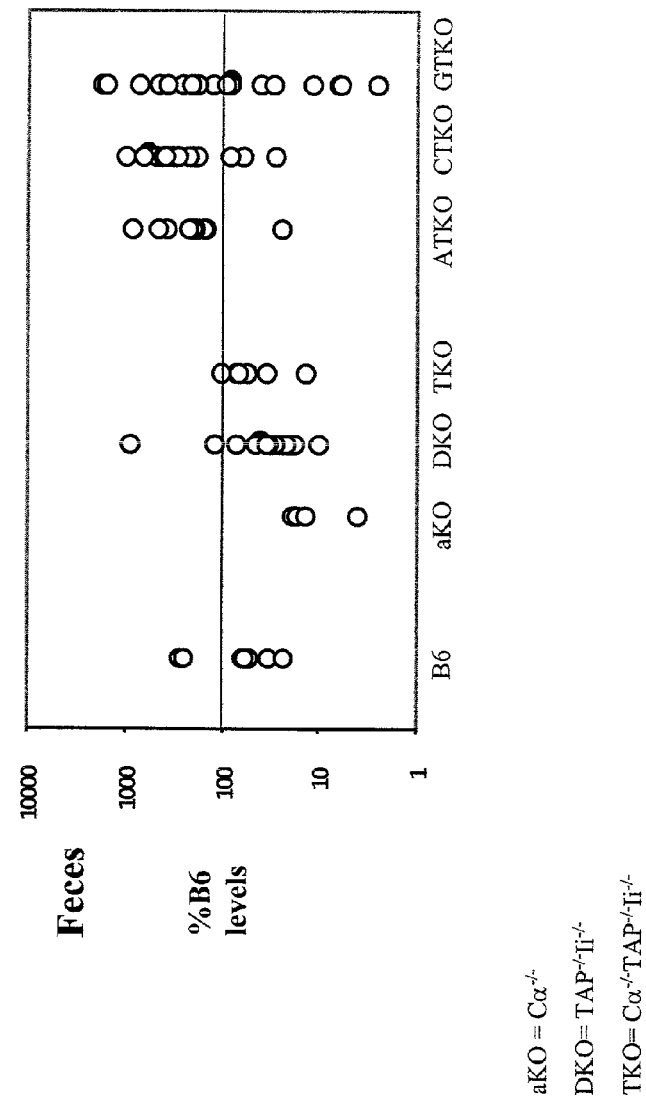
Figure 5B:
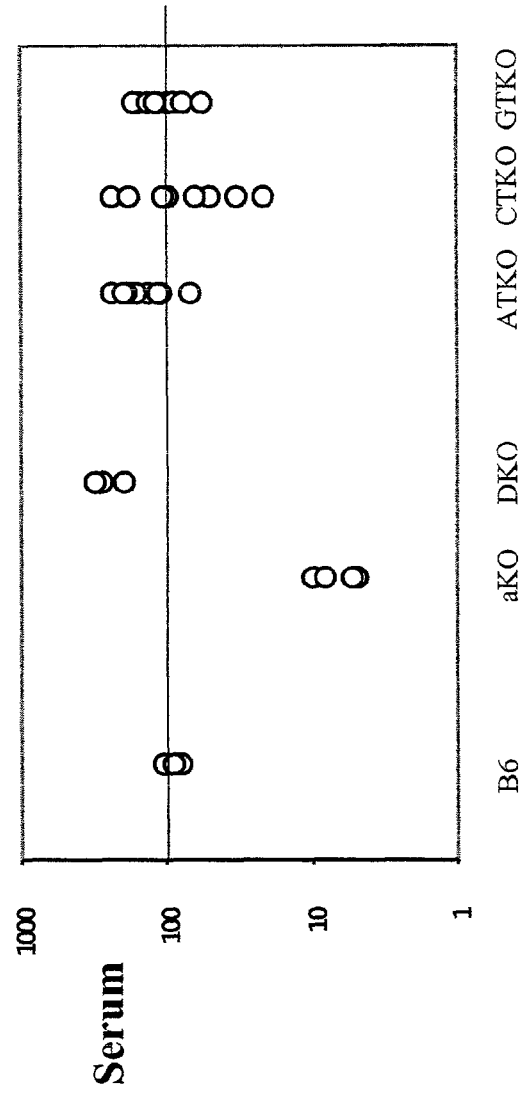
Figure 5C:
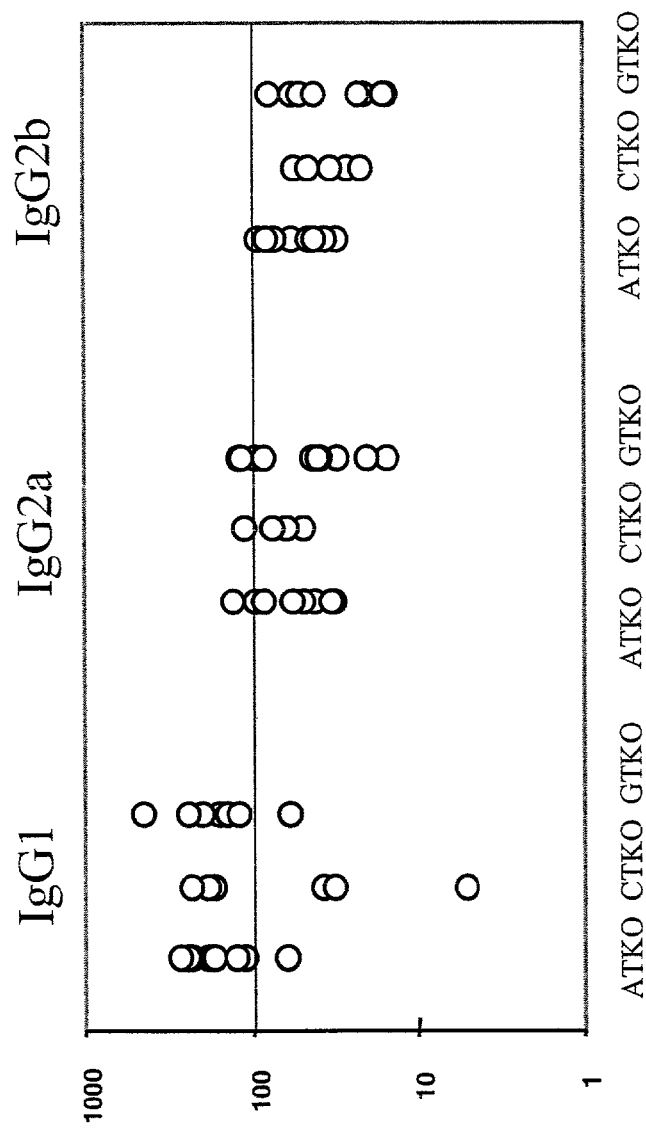

The modifications in the LP B cell phenotype observed according to the amount of MAIT cells suggested that these cells may regulate gut B cell functions. Indeed, a large increase (3 to 10 folds) of IgA levels was found in the feces of the Cα$^{-/-}$/TAP$^{-/-}$/Ii$^{-/-}$ Vα19-Jα33 Tg mice as compared to B6 animals (FIG. 5A). One possible caveat of this finding was that Cα deficient mice are prone to develop a colitis which could account for the phenotype of the Vα19-Jα33 Tg mice, which are either on a Cα$^{-/-}$ or a Ca$^{-/-}$/TAP$^{-/-}$/Ii$^{-/-}$ background. However, we found no increase in feces IgA levels in Cα$^{-/-}$, TAP$^{-/-}$/Ii$^{-/-}$ or Cα$^{-/-}$/TAP$^{-/-}$/Ii$^{-/-}$ mice bred in our animal facility. Furthermore, histology analysis of gut sections of 4/5 months old Vx19-Jα33 Tg mice in both backgrounds showed no signs of colitis (not shown). Thus, the gut IgA overproduction we observe is certainly linked to the over-expression of MAIT cells in the Vα19-Jα33 Tg mice. On the other hand, the serum levels of the different Ig isotypes were similar in the Tg and B6 mice indicating the absence of skewing towards Th1 (IgG2a) or Th2 (IgG1, IgE) of the systemic immune response in Vα19-Jα33 Tg mice. There was only a slight increase in IgG1 levels, and a small decrease in IgG2b levels, while IgG2a, IgE and IgA levels were similar (FIG. 5B). Thus, MAIT cell over-expression modified only the intestinal IgA and not the serum Ig levels.

Figure 5D:
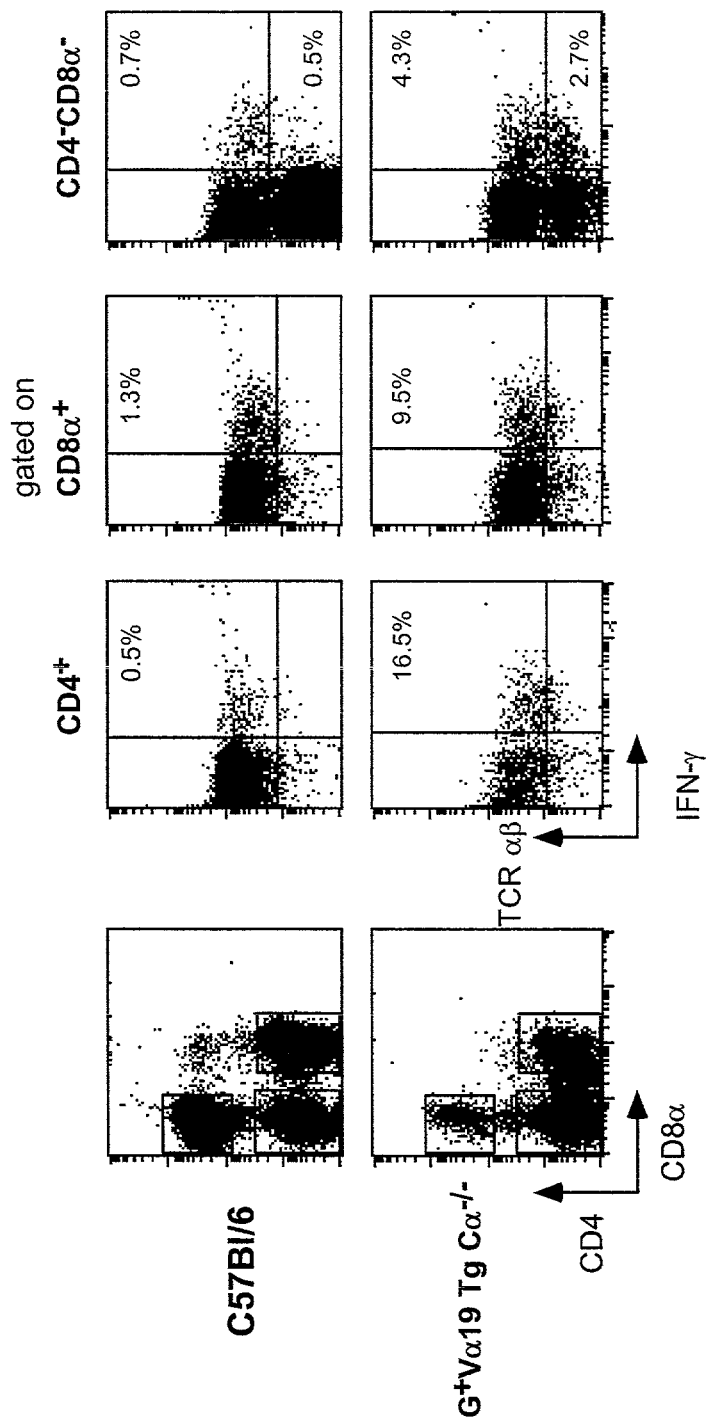
Figure 5E:
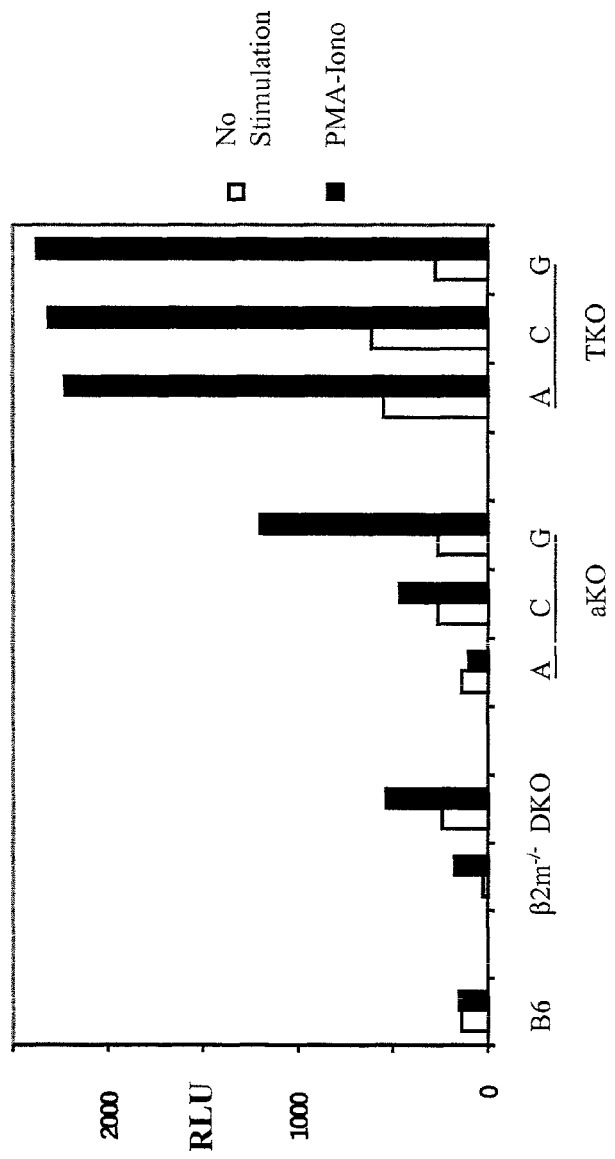
Figure 5F:
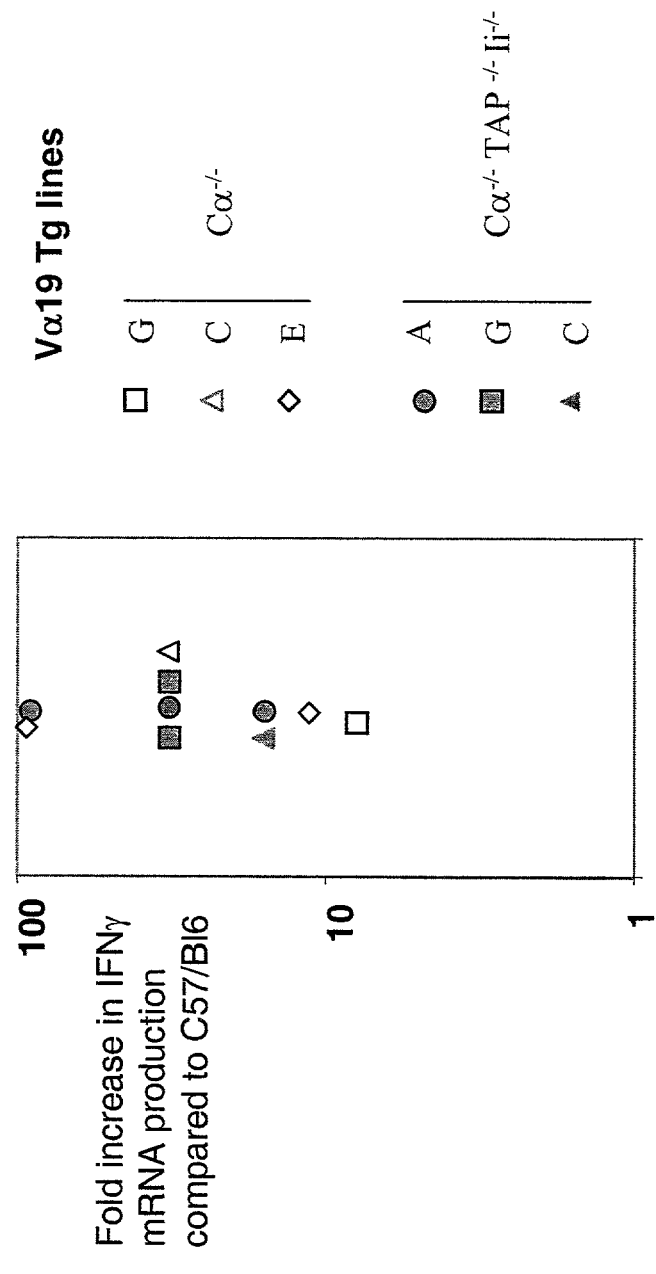

To further define the mechanisms involved in this increased intestinal IgA secretion seen in MAIT cell over-expressing mice, we measured the lymphokines expressed or produced by MAIT cells after different stimuli. We first stimulated Vα19-Jα33 Tg MLN T cells with PMA and Ionomycine and examined their cytokine production by intracellular staining or in the supernatant. The proportion of CD4$^+$ and CD8$^+$ TCRαβ$^+$ cells secreting IFN-γ was increased in the Tg mice when compared to B6 controls (CD4$^+$: 10%+/− vs; CD8$^+$: 7%+/− vs 1%+/−) (FIG. 5C), while that of IL4 and IL10 producing cells was similar (data not shown). Importantly, the amount of the main lymphokine involved in IgA secretion, TGFβ1 was increased in the supernatant of activated Vα19-Jα33 Tg MLN T cells (FIG. 5D). The mRNA of several cytokines extracted from Tg LPL was also measured by Q-PCR. Tg mice displayed an average 10-fold increase in IFN-γ mRNA levels when compared to control mice, while those of IL4 were decreased by 2-fold (FIG. 5E). On the other hand, IL-5, IL2, IL10 and TNF-α mRNA levels expression were similar in wt and in Vα19-Jα33 Tg mice (data not shown). As IFN-γ has been implicated in the up-regulation of poly Ig receptor (pIgR) which transports IgA from the interstitium to the intestinal lumen, this increased IFN-γ expression associated with the higher TGFβ1 secretion observed in Vα19-Jα33 Tg mice suggest that the MAIT cell have the ability to stimulate intestinal IgA secretion.

MAIT Cells and MR1

Figure 6A:
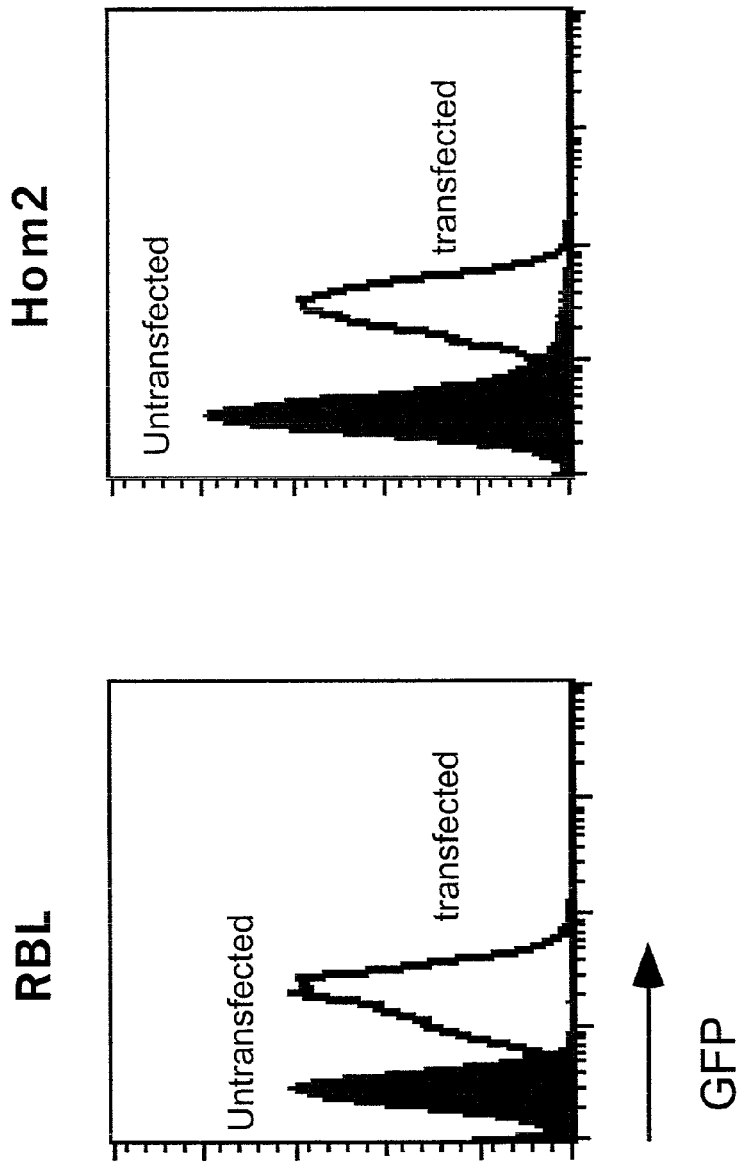
Figure 6B:
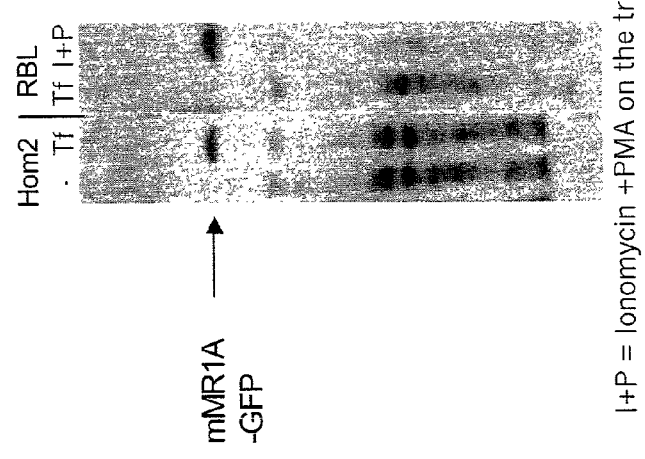
Figure 6C:
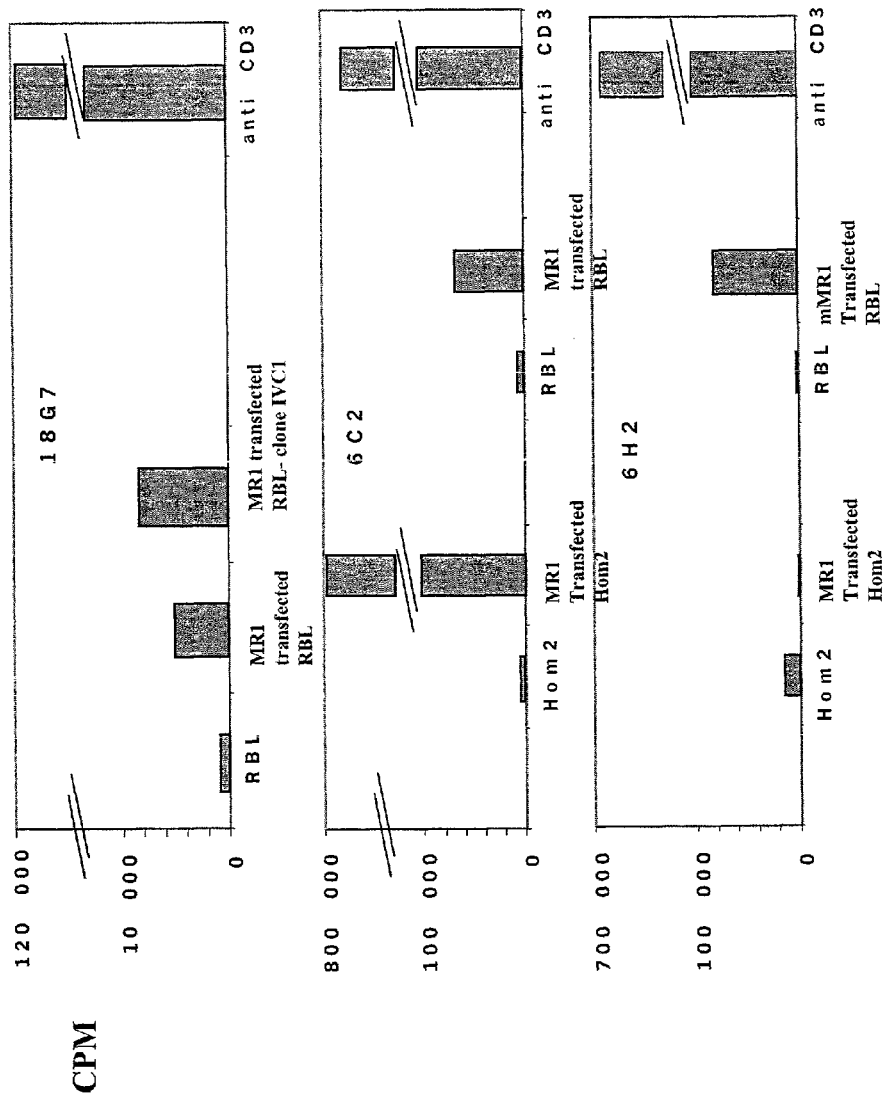
Figure 6D:
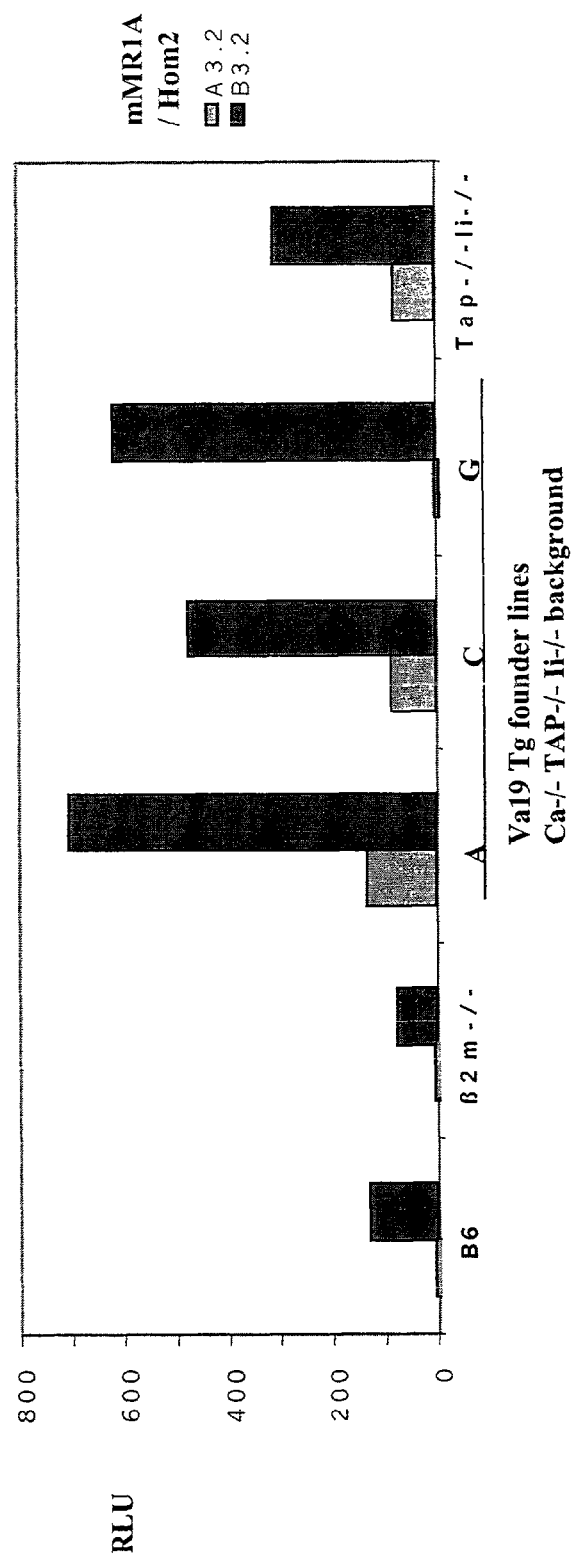

As the MAIT cells require hematopoietic and more specifically B cells for their selection (see companion paper), we first examined the ability of a panel of cell lines to stimulate a series of T-T hybridoma expressing the Vα19-Jα33$^+$ TCR (Tilloy et al., J. Exp. Med., 1999, 1907-1921 and unpublished data). None of the lines studied were able to induce the release of IL-2 by more than 40 T-T hybridoma tested (data not shown). The striking phylogenetic conservation of both MR1 and MAIT TCR sequences made of MR1 a good candidate to be the ligand of MAIT cells. We generated several lines expressing mMR1A as a fusion protein with EGFP. As displayed in FIG. 6A, the transfectants were GFP-positive by FACS but most of the fluorescence was inside the cell (data not shown), similarly to what has been described in another instance (BBRC). In a transfected human B cell line (HOM2), a small amount of the protein was expressed at the cell surface as shown by the 80 kD band seen in the western blot with anti-GFP antibody on a streptavidin bead precipitate of a surface biotinylated cell lysate (FIG. 6B). As for transfected RBL, surface expression was seen only after stimulation with ionomycine and a phorbol ester (FIG. 6B). We then examined the ability of these MR1 transfectants to stimulate the T-T hybridoma. As shown in FIG. 6C, 3 hybridomas, were specifically stimulated to release IL-2 by the MR1A-transfected RBL (18G7, 6C2, 6H2) and/or by HOM2 (6C2), strongly suggesting that there was a direct recognition of MR1A by the Vα19-Jα33 TCR. In accordance with these results, T cells obtained from Vα19-Jα33 TCR transgenic mice which overexpress MAIT cells were stimulated to release TGFβ1 by the HOM2 transfectants (FIG. 6D). However, in the absence of a blocking antibody, we cannot formally exclude that the 3 hybridomas and the Tg T cells were in fact recognizing an MR1-derived peptide presented by RBL or HOM2 endogenous MHC.

Figure 7A:
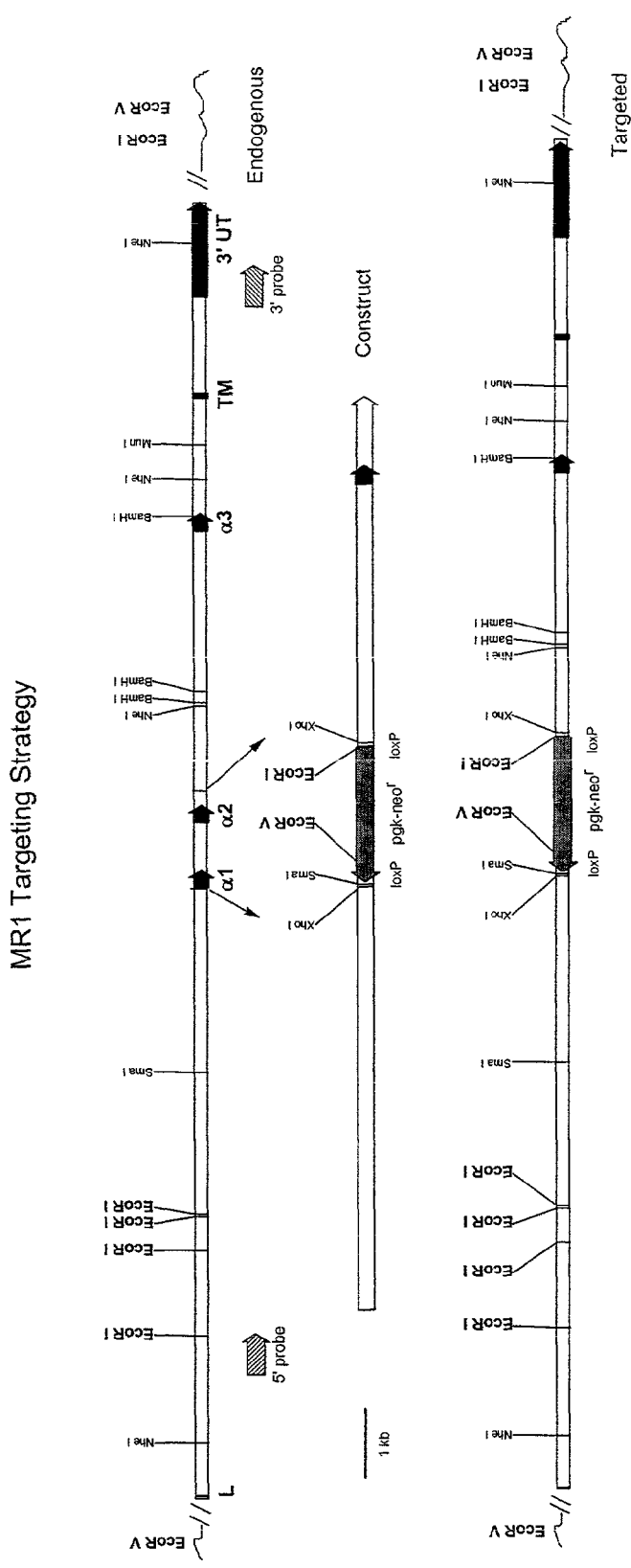
Figure 7B:
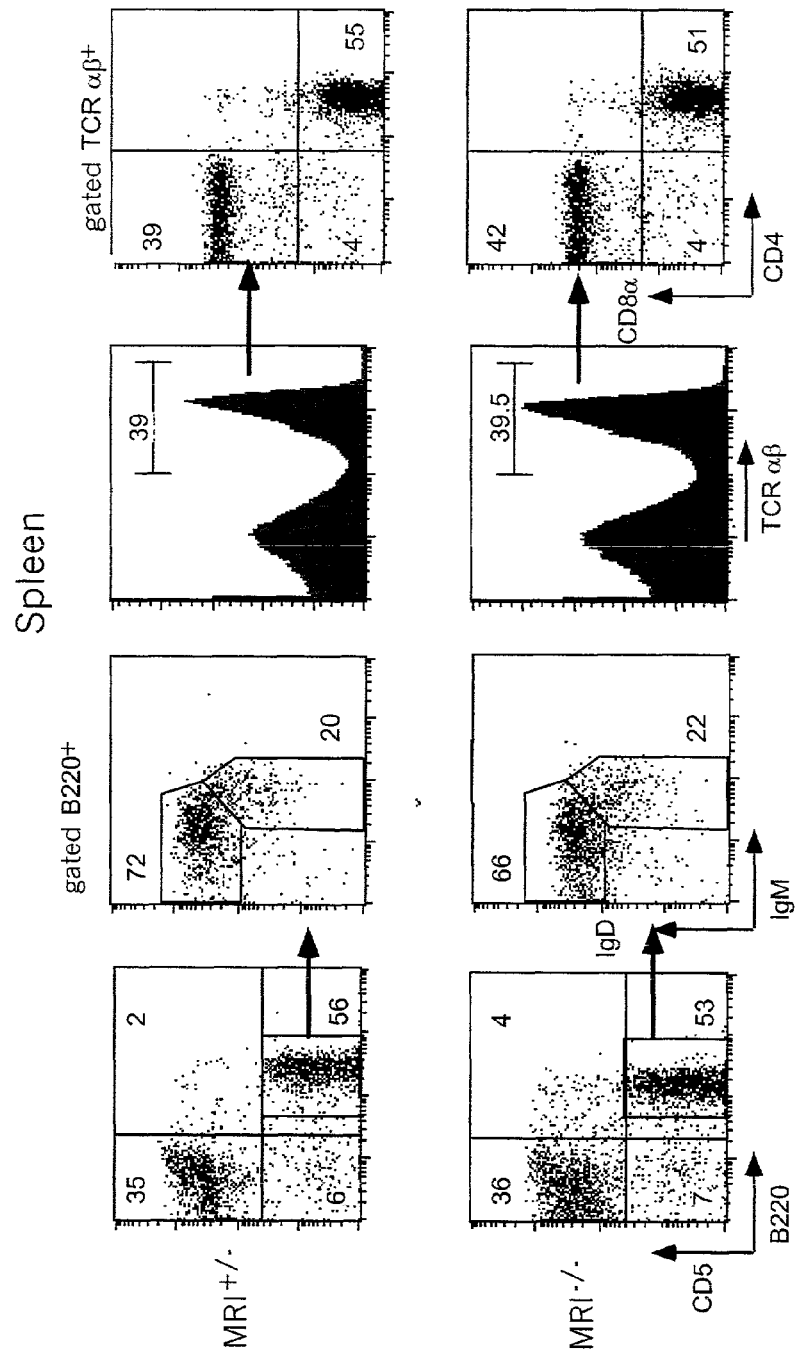
Figure 7C:
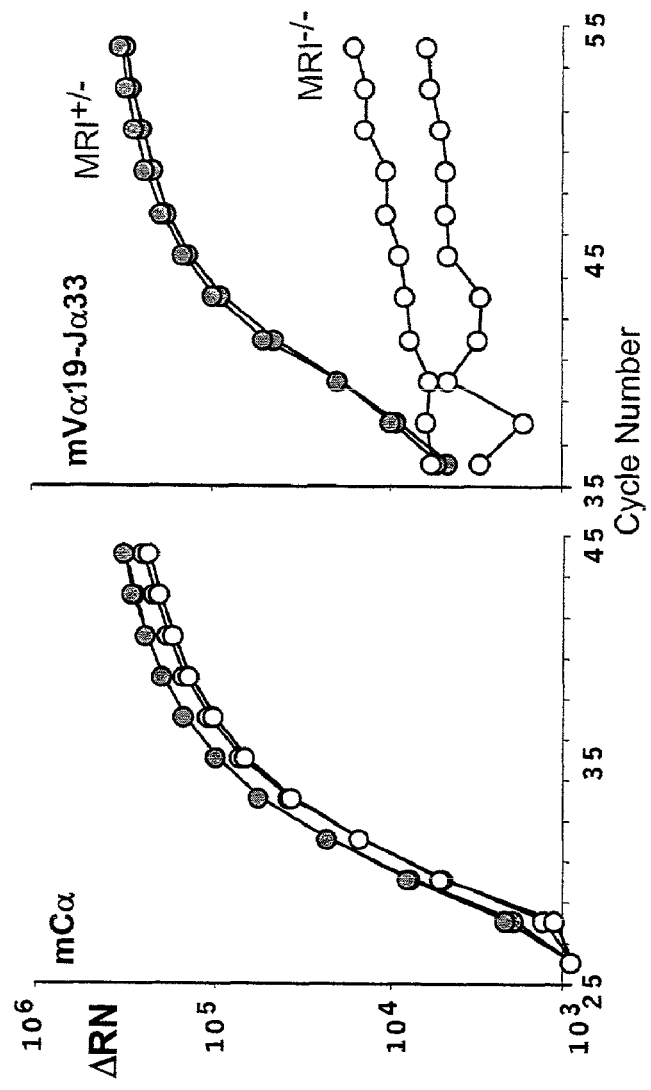

Thus, to demonstrate the role of MR1A in the in vivo selection of MAIT cells, we studied a MR1 deficient mouse generated by S. Gilfillan and S. Barham. The targeting strategy is displayed in FIG. 7A. MR1 KO mice displayed normal number and phenotype of T and B cells in central and peripheral lymphoid organs (thymus, spleen, peripheral and mesenteric lymph nodes (PLN and MLN) (FIG. 7B). Using real-time RT-PCR for Vα19-Jα33 segments on sorted TCR αβ+DN from MLN, we were not able to amplify any Vα19-Jα33 sequence in MR1 KO mice, while a normal amplification was obtain in littermate controls (FIG. 7C). Polyclonal sequencing of the Vα19-Jα33 amplicons confirmed the specificity of the amplification (data not shown). The same result was obtained on LP T cells (FIG. 7D). Thus, Vα19-Jα33 expressing MAIT cells are absent from MR1 KO mice. Altogether, these results demonstrate that MR1 is the ligand, which selects the MAIT cells.

The invention claimed is:

1. A method of selecting, screening or characterizing a compound, wherein said method comprises contacting a test compound with Vα7.2-Jα33 or Vα19-Jα33 T cells or specific TCR thereof in the presence of MR1A and determining the ability of said test compound to increase the binding of said MR1A to said cells or TCR.

2. A method of selecting, screening or characterizing a compound, said method comprises contacting a test compound with Vα7.2-Jα33 or Vα19-Jα33 T cells in the presence of MR1A polypeptide or a host cell expressing a MR1A polypeptide, and determining the ability of said test compound to increase a biological response induced by MR1A polypeptide.

3. The method of claim 2, wherein the biological response is selected from the group consisting of activation of LP B cell, increase of the expressed levels of IgA, a cytolytic activity, and an increase of IFN-γ or TGFβ secretion.

4. The method of claim 2, wherein the host cell expressing a MR1A polypeptide is a LP B-cell expressing a MR1A polypeptide.

5. The method of claim 4, wherein the biological response is selected in the group consisting of activation of said B cells, an increase of the expressed levels of IgA, a cytolytic activity, and an increase of IFN-γ or TGFβ secretion.

* * * * *

SEQUENCE LISTING

```
<160> NUMBER OF SEQ ID NOS: 5

<210> SEQ ID NO 1
<211> LENGTH: 341
<212> TYPE: PRT
<213> ORGANISM: Homo sapiens

<400> SEQUENCE: 1

Met Gly Glu Leu Met Ala Phe Leu Leu Pro Leu Ile Ile Val Leu Met
1               5                   10                  15

Val Lys His Ser Asp Ser Arg Thr His Ser Leu Arg Tyr Phe Arg Leu
            20                  25                  30

Gly Val Ser Asp Pro Ile His Gly Val Pro Glu Phe Ile Ser Val Gly
        35                  40                  45

Tyr Val Asp Ser His Pro Ile Thr Thr Tyr Asp Ser Val Thr Arg Gln
    50                  55                  60

Lys Glu Pro Arg Ala Pro Trp Met Ala Glu Asn Leu Ala Pro Asp His
65                  70                  75                  80

Trp Glu Arg Tyr Thr Gln Leu Leu Arg Gly Trp Gln Gln Met Phe Lys
                85                  90                  95

Val Glu Leu Lys Arg Leu Gln Arg His Tyr Asn His Ser Gly Ser His
            100                 105                 110

Thr Tyr Gln Arg Met Ile Gly Cys Glu Leu Leu Glu Asp Gly Ser Thr
        115                 120                 125

Thr Gly Phe Leu Gln Tyr Ala Tyr Asp Gly Gln Asp Phe Leu Ile Phe
    130                 135                 140

Asn Lys Asp Thr Leu Ser Trp Leu Ala Val Asp Asn Val Ala His Thr
145                 150                 155                 160

Ile Lys Gln Ala Trp Glu Ala Asn Gln His Glu Leu Leu Tyr Gln Lys
                165                 170                 175

Asn Trp Leu Glu Glu Cys Ile Ala Trp Leu Lys Arg Phe Leu Glu
            180                 185                 190

Tyr Gly Lys Asp Thr Leu Gln Arg Thr Glu Pro Pro Leu Val Arg Val
        195                 200                 205

Asn Arg Lys Glu Thr Phe Pro Gly Val Thr Ala Leu Phe Cys Lys Ala
    210                 215                 220

His Gly Phe Tyr Pro Pro Glu Ile Tyr Met Thr Trp Met Lys Asn Gly
225                 230                 235                 240

Glu Glu Ile Val Gln Glu Ile Asp Tyr Gly Asp Ile Leu Pro Ser Gly
                245                 250                 255

Asp Gly Thr Tyr Gln Ala Trp Ala Ser Ile Glu Leu Asp Pro Gln Ser
            260                 265                 270
```

```
Ser Asn Leu Tyr Ser Cys His Val Glu His Cys Gly Val His Met Val
        275                 280                 285

Leu Gln Val Pro Gln Glu Ser Glu Thr Ile Pro Leu Val Met Lys Ala
        290                 295                 300

Val Ser Gly Ser Ile Val Leu Val Ile Val Leu Ala Gly Val Gly Val
305                 310                 315                 320

Leu Val Trp Arg Arg Arg Pro Arg Glu Gln Asn Gly Ala Ile Tyr Leu
                325                 330                 335

Pro Thr Pro Asp Arg
            340

<210> SEQ ID NO 2
<211> LENGTH: 41
<212> TYPE: DNA
<213> ORGANISM: Mus musculus

<400> SEQUENCE: 2
aagaaggaga tctgtgatgg tgctcctgtt acctctgctc g                41

<210> SEQ ID NO 3
<211> LENGTH: 41
<212> TYPE: DNA
<213> ORGANISM: Mus musculus

<400> SEQUENCE: 3
agagaaagaa ttcgagaggg agagcttccc tcattcactt g                41

<210> SEQ ID NO 4
<211> LENGTH: 41
<212> TYPE: DNA
<213> ORGANISM: Homo sapiens

<400> SEQUENCE: 4
aaaaaatttc cgctagcggg atgggggaac tgatggcgtt c                41

<210> SEQ ID NO 5
<211> LENGTH: 41
<212> TYPE: DNA
<213> ORGANISM: Homo sapiens

<400> SEQUENCE: 5
tttttaaccc tcgagtcgat ctggtgttgg aaggtagatg g                41
```